US012805503B1

(12) United States Patent
Petersen et al.

(10) Patent No.: US 12,805,503 B1
(45) Date of Patent: *Nov. 24, 2026

(54) LIVESTOCK FOOTBATH SOLUTIONS AND METHODS OF USE

(71) Applicant: Specialty Sales, LLC, Fresno, CA (US)

(72) Inventors: Greg Petersen, Fresno, CA (US); Gerald Byrd, Kirkland, WA (US); Don Alsup, Fresno, CA (US); Shawn Pendergast, Fresno, CA (US)

( * ) Notice: Subject to any disclaimer, the term of this patent is extended or adjusted under 35 U.S.C. 154(b) by 385 days.

This patent is subject to a terminal disclaimer.

(21) Appl. No.: 18/225,602

(22) Filed: Jul. 24, 2023

Related U.S. Application Data

(63) Continuation-in-part of application No. 18/135,476, filed on Apr. 17, 2023, now abandoned, which is a (Continued)

(51) Int. Cl.

| | |
|---|---|
| ***A01L 15/00*** | (2006.01) |
| ***A01K 13/00*** | (2006.01) |
| ***A61K 9/08*** | (2006.01) |
| ***A61K 31/194*** | (2006.01) |
| ***A61K 33/30*** | (2006.01) |
| ***A61K 33/34*** | (2006.01) |

(52) U.S. Cl.

CPC ............ *A01L 15/00* (2013.01); *A01K 13/001* (2013.01); *A01K 13/003* (2013.01); *A61K 9/08* (2013.01); *A61K 31/194* (2013.01); *A61K 33/30* (2013.01); *A61K 33/34* (2013.01)

(58) Field of Classification Search

None

See application file for complete search history.

(56) References Cited

U.S. PATENT DOCUMENTS 2,299,604 A 10/1942 Welrich
2,965,565 A 12/1960 McDonald
(Continued)

FOREIGN PATENT DOCUMENTS

CA 1218302 2/1987
DE 4439572 5/1996
(Continued)

OTHER PUBLICATIONS

Jessica Light (dailywellness.com, Oct. 2014).
(Continued)

*Primary Examiner* — Dominic Lazaro

(74) *Attorney, Agent, or Firm* — Sierra IP Law, PC; William K. Nelson

(57) ABSTRACT

Embodiments of the present invention provide improved livestock foot bath solutions that are capable of maintaining a low pH during longer periods of use in order to help prevent the metal salts from precipitating out of the solution and rendering the solution ineffective. Embodiments of the present invention provide improved livestock foot bath solutions that include one or more weak organic acids, such as polyprotic organic acids, in the aqueous solution, along with the dissolved metal salts. Embodiments of the invention may also include sulfuric acid, or some other strong acid, together with citric acid and the dissolved metal salts in the aqueous solution.

21 Claims, 34 Drawing Sheets

Related U.S. Application Data continuation of application No. 18/100,576, filed on Jan. 24, 2023, now abandoned, which is a continuation of application No. 15/713,534, filed on Sep. 22, 2017, now Pat. No. 11,559,053.

(60) Provisional application No. 62/398,828, filed on Sep. 23, 2016.

(56) References Cited

U.S. PATENT DOCUMENTS

| | | | | |
|---|---|---|---|---|
| 4,008,332 | A | 2/1977 | Thomas | |
| 4,164,477 | A | 8/1979 | Whitley | |
| 4,268,504 | A | 5/1981 | Harrington | |
| 4,299,613 | A | 11/1981 | Cardarelli | |
| 4,859,694 | A | 8/1989 | Pavlich | |
| RE33,512 | E | 1/1991 | Ramirez | |
| 5,203,366 | A | 4/1993 | Czeck | |
| 5,480,643 | A | 1/1996 | Donovan | |
| 5,630,379 | A | 5/1997 | Gerk | |
| 5,648,389 | A | 7/1997 | Gans | |
| 5,692,570 | A | 12/1997 | Akesson | |
| 5,772,985 | A | 6/1998 | Kemp | |
| 5,967,202 | A | 10/1999 | Mullen | |
| 5,998,483 | A | 12/1999 | Camiener | |
| 6,003,469 | A | 12/1999 | Sherwood | |
| 6,093,422 | A | 7/2000 | Denkewicz, Jr. | |
| 6,183,785 | B1 | 2/2001 | Westfall | |
| 6,294,186 | B1 | 9/2001 | Beerse | |
| 6,344,218 | B1 | 2/2002 | Dodd | |
| 6,364,025 | B1 | 4/2002 | Jacobs | |
| 6,375,976 | B1 | 4/2002 | Roden | |
| 6,382,136 | B1 | 5/2002 | Bragulla | |
| 6,444,707 | B1 | 9/2002 | Lampe | |
| 6,596,325 | B1 | 7/2003 | Vroom | |
| 6,617,296 | B1 | 9/2003 | Connors | |
| 6,863,898 | B2 | 3/2005 | Clawson | |
| 7,097,861 | B1 | 8/2006 | O'Brien | |
| 7,332,151 | B2 | 2/2008 | Yoder | |
| 7,533,733 | B2 | 5/2009 | Nolan | |
| 7,661,393 | B2 | 2/2010 | Torgerson | |
| 7,670,629 | B2 | 3/2010 | Baltzell | |
| 7,798,104 | B2 | 9/2010 | Rajkondawar | |
| 7,841,299 | B2 | 11/2010 | Gerk | |
| 7,987,820 | B2 | 8/2011 | Eakin | |
| 8,389,581 | B2 | 3/2013 | DeMarco | |
| 9,010,277 | B2 | 4/2015 | Eakin | |
| 9,018,262 | B2 | 4/2015 | DeMarco | |
| 11,559,053 | B1 * | 1/2023 | Petersen | A01K 13/003 |
| 2003/0083222 | A1 | 5/2003 | Raso | |
| 2004/0175433 | A1 | 9/2004 | Thomson | |
| 2004/0176312 | A1 | 9/2004 | Gillis | |
| 2004/0198639 | A1 | 10/2004 | Patt | |
| 2007/0074672 | A1 | 4/2007 | Torgerson | |
| 2008/0121189 | A1 | 5/2008 | Greeson | |
| 2008/0166424 | A1 | 7/2008 | Mixon | |
| 2009/0110751 | A1 | 4/2009 | Kenneke | |
| 2009/0178626 | A1 | 7/2009 | Greeson | |
| 2010/0234460 | A1 | 9/2010 | Foret | |
| 2010/0286270 | A1 * | 11/2010 | Foret | A61K 31/60 514/568 |
| 2015/0366819 | A1 | 12/2015 | DeMarco | |

FOREIGN PATENT DOCUMENTS

| | | | | |
|---|---|---|---|---|
| GB | 2110084 | | 6/1983 | |
| GB | 2141929 | A | 1/1985 | |
| WO | WO-2007070655 | A2 * | 6/2007 | A61K 33/24 |
| WO | 2009053934 | A2 | 4/2009 | |

OTHER PUBLICATIONS

Hauptmeier, Larry; Brown, Paul, "Foot Rot in Beef Cattle", Article retrieved on Jun. 19, 2019 from "https://store.extension.iastate.edu/product/Foot-Rot-in-Beef-Cattle".

Abbott, KA; Lewis, CJ. , "Current approaches to the management of ovine footrot.", Abstract retrieved on Jun. 19, 2019 from "https://www.ncbi.nlm.nih.gov/pubmed/15683762".

Cook, NB; "Foot Bath Operation for the control of Infectious Diseases of the Hoof in Dairy Cattle", Article retrieved on Jun. 19, 2019 from "http://www.hachaklait.org.il/files/430806.pdf".

Gradin, JL; Schmitz, JA, "Susceptibility of Bacteroides nodosus to various antimicrobial agents.", Abstract retrieved on Jun. 19, 2019 from "https://europepmc.org/abstract/med/6618969".

Jelinek, PD; Depiazzi, LJ, "Failure to eradicate ovine footrot associated with Dichelobacter nodosus strain A198 by repeated daily footbathing in zinc sulphate with surfactant.", Abstract retrieved on Jun. 19, 2019 from "https://www.ncbi.nlm.nih.gov/pubmed/15084013".

Jelinek, PD; Depiazzi, LJ; Galvin, DA; Spicer, IT; Palmer, MA; Pitman, DR., "Eradication of ovine footrot by repeated daily footbathing in a solution of zinc sulphate with surfactant.", Abstract retrieved on Jun. 19, 2019 from "https://www.ncbi.nlm.nih.gov/pubmed/11491224".

Kimberling, CV; Ellis, RP, "Advances in the control of foot rot in sheep.", Abstract retrieved on Jun. 19, 2019 from "https://www.ncbi.nlm.nih.gov/pubmed/2245368".

Laven, RA; Hunt, H, "Evaluation of copper sulphate, formalin and peracetic acid in footbaths for the treatment of digital dermatitis in cattle.", Abstract retrieved on Jun. 19, 2019 from "https://www.ncbi.nlm.nih.gov/pubmed/12199433".

Malecki JC; McCausland IP, "In vitro penetration and absorption of chemicals into the ovine hoof.", Abstract retrieved on Jun. 20, 2019 from "https://www.ncbi.nlm.nih.gov/pubmed/7146628".

Malecki, JC; Coffey, L; "Treatment of ovine virulent footrot with zinc sulphate/sodium lauryl sulphate footbathing.", Abstract retrieved on Jun. 20, 2019 from "https://www.ncbi.nlm.nih.gov/pubmed/3439946".

Ortolani, EL; Antonelli, AC; de Souza Sarkis, JE, "Acute sheep poisoning from a copper sulfate footbath.", Abstract retrieved on Jun. 20, 2019 from "https://www.ncbi.nlm.nih.gov/pubmed/15587248".

Parajuli, B; Goddard, PJ, "A comparison of the efficacy of footbaths containing formalin or zinc sulphate in treating ovine foot-rot under field conditions." , Abstract retrieved on Jun. 20, 2019 from "https://www.ncbi.nlm.nih.gov/pubmed/2790439".

Reed, GA; Alley, DU, "Efficacy of a novel copper-based footbath preparation for the treatment of ovine footrot during the spread period." , Abstract retrieved on Jun. 20, 2019 from "https://www.ncbi.nlm.nih.gov/pubmed/8941419".

Shearer, JK; van Amstel, SR, "Managing Lameness for Improved Cow Comfort and Performance" , Article retrieved on Jun. 20, 2019 from "http://wdmc.org/2003/Managing%20Lameness%20for%20Improved%20Cow%20Comfort%20and%20Performance.pdf".

Skerman, TM; Green, RS; Hughes, JM; Herceg, M , "Comparison of footbathing treatments for ovine footrot using formalin or zinc sulphate.", Abstract retrieved on Jun. 20, 2019 from "https://www.ncbi.nlm.nih.gov/pubmed/16030968".

Skerman, TM; Moorhouse, SR; Green, RS, "Further investigations of zinc sulphate footbathing for the prevention and treatment of ovine footrot.", Abstract extract retrieved on Jun. 20, 2019 from "https://www.tandfonline.com/doi/abs/10.1080/00480169.1983.34981".

Whittier, WD; Umberger, SH, "Control, Treatment, and Elimination of Foot Rot from Sheep" , Article retrieved on Jun. 20, 2019 from "https://www.pubs.ext.vt.edu/content/dam/pubs_ext_vt_edu/410/410-028/410-028_pdf.pdf".

Cook, NB; "Footbath Alternatives" , Article retrieved on Jun. 24, 2019 from https://hoofzink.com/wp-content/uploads/2015/05/footbath-alternatives.pdf.

Kempson et al, "Use of Topical Disinfectant as part of a hoof care programme for horses with diseases of the hoof capsule." Veterinary Record, British Veterinary Association, London, GB, vol. 154, No. 21, May 22, 2004: 647-652.

(56) References Cited

OTHER PUBLICATIONS

Manske et al. "Topical treatment of digital dermatitis associated with severe heel-horn erosion in a Swedish dairy herd." Preventative Veterinary Medicine, vol. 53, No. 3, (2002): 215-231.
Thomsen et al., "Evaluation of Three Commercial Hoof Care Products Used in Footbaths in Danish Dairy Herds." Journal of Dairy Science, vol. 91, No. 4 (2008): 1361-1365.
Bedino, James, "Embalming Chemistry: Glutaraldehyde versus Formaldehyde." Expanding Encyclopedia of Mortuary Practices, No. 649. Springfield, The Chamption Company, (2003), 2614-2632.
Glyoxal Cas No. 107-22-2, SIDS Initial Assessment Profile, UNEP Publications, (2006): 123-178.
English Abstract of DE4439572, retrieved Apr. 10, 2023 from.

* cited by examiner

LIVESTOCK FOOTBATH SOLUTIONS AND METHODS OF USE

PRIORITY CLAIM

This application is continuation-in-part of U.S. application Ser. No. 18/135,476, filed on Apr. 17, 2023, which is a continuation of Ser. No. 15/713,534, filed on Sep. 22, 2017, which is a non-provisional of and claims the benefit of U.S. Provisional Application No. 62/398,828 filed on Sep. 23, 2016. The present application claims priority to and incorporates by reference each of the above-mentioned applications.

BACKGROUND OF THE INVENTION

The present invention relates to footbaths used to clean the hooves of livestock, and more particularly to improved solutions for use in livestock footbaths and related methods of use.

Footbaths are used in the management of livestock, particularly dairy cattle, to clean the hooves of the livestock by killing bacteria, viruses, fungi, and other pathogens, and to generally maintain the health and hardening of the hooves. Solutions provided in livestock footbaths may also be used to deliver treatments for such things as foot-rot, heel erosion, digital dermatitis and the like. It is to be appreciated that many foot diseases can lead to unhealthy livestock, and can result in diminished or unusable milk production in dairy cows.

Existing livestock footbath solutions typically contain metallic salts that include copper sulfate ions ($CuSO_4$) and/or zinc sulfate ions ($ZnSO_4$), which are effective in eliminating pathogens that may be detrimental to hoof health. It is known that aqueous solutions of these salts generally start with a pH of between about 4.2 and about 5.0, and that salts of these metals tend to precipitate from solution above a pH of about 5.0, rendering the solutions less effective in combating pathogens. For this reason, a typical dairy farmer will strive to keep the pH of the footbath solution at or below about 4.5 to prevent precipitation and keep the ions in solution.

All footbath compositions have a problem with maintaining a pH of 4.5 or less to keep the metallic salts soluble and therefore at maximum ionization. This is because during use alkaline waste from the livestock that pass through a footbath has the effect of raising the pH of the footbath solution. As a result, in order to neutralize the waste and keep the pH down, and thereby keep the metal ions solubilized in the aqueous solution, it is a common practice to add a strong mineral acid, such as sulfuric acid ($H_2SO_4$) to the solution. However, because of the corrosive nature of sulfuric acid, it is necessary to keep the acid at a low level in the footbath solution. Since only a limited amount of sulfuric acid may be safely added to a footbath solution, it can only neutralize a limited amount of animal waste before the pH of the solution will start rising. Thus, even with the addition of sulfuric acid, the pH of the footbath solution will eventually rise above the target of 4.5, resulting in precipitation of the needed metal salts, and rendering the solution ineffective for eliminating pathogens.

It is not unusual to find a dairy footbath registering a pH of 5-6 after the passage of 500 cows. Because of this, it is common for suppliers of footbath compositions to recommend adding additional doses of sulfuric acid or other buffers such as sodium sulfate and sodium bisulfate to extend the life of the footbath solution, or to replace a dairy footbath solution after every 250 cows. However, even with the use of multiple buffers, foot bath compositions tend to quickly meet or exceed pH levels accepted by the industry.

Unfortunately, adding doses of sulfuric acid or buffers to an existing footbath solution can be tricky, time consuming and labor intensive. It is desirable to know the pH of the solution in order to determine whether any sulfuric acid or buffering is needed, and if so, how much. However, it is often difficult to obtain an accurate pH reading of a dirty footbath that is in use, which may result in the addition of too much sulfuric acid, which may be hazardous to the animals, or too little sulfuric acid which may be ineffective in improving the pH of the solution. This leaves replacing the solution as the only reliable alternative. However, given the speed at which cows are milked in modern dairy systems, a changing the footbath solution after every 250 cows is impractical if not impossible, not to mention expensive and time consuming in terms of both solution cost and labor.

It is therefore desirable to provide improved livestock foot bath solutions that are capable of maintaining a low pH during longer periods of use in order to keep the metal salts from precipitating out of the solution.

SUMMARY OF THE INVENTION

The present invention addresses this problem by providing improved livestock foot bath solutions that include one or more weak organic acids or salts thereof (e.g., polyprotic organic acids or salts thereof), such as citric acid, succinic acid, 2,3 dihydroxylated succinic acid, glutaric acid, hexanedioic acid, heptanedioic acid, octanedioic acid, nonanedioic acid, decanedioic acid, malic acid, fumaric acid, aconitic acid, Isocitric acid, Propane-1,2,3-tricarboxylic acid, benzene-1,3,5-tricarboxylic acid, benzene-1,3,5-tricarboxylic acid, salts of such organic acids, and combinations thereof, in the aqueous solution, along with the dissolved metal salts. Embodiments of the invention may also include sulfuric acid, or some other strong acid, together with citric acid and the dissolved metal salts in the aqueous solution. Those skilled in the art have dismissed the use of organic acids such as polyprotic acids to reduce pH levels in livestock foot bath solutions because they are weak acids, preferring instead to use a strong acid such as sulfuric acid, or the like, for this purpose. However, even though a weak organic acids, particularly polyprotic organic acids like citric acid, may not themselves have a dramatic effect on reducing the pH of a foot bath solution, they may have the effect of buffering a foot bath solution of metal salts (including copper and zinc) such that a significant amount of alkali/basic material is required to raise the pH of such a solution above the target of 4.5. This effect may be increased by adding a strong acid, such as sulfuric acid, with one or more weak organic acids or salts thereof (e.g., citric acid) as identified herein in the foot bath solution. As demonstrated by the examples herein, aqueous solutions of metal salts of copper and zinc which also contain polyprotic organic acid are able to receive roughly twice the amount of alkali/base as similar solutions that do not contain polyprotic acid before reaching a pH of 4.5. The footbath solution is a solution (in contrast to a colloidal mixture or other heterologous composition) having low viscosity (e.g., in a range of about 0.85 centipoise to about 1.1 centipoise at stand STP conditions). In use, these solutions are capable of treating approximately 500 dairy cows before the solution needs to be changed, amended or replaced, which effectively doubles the useful life of a foot bath solution, resulting in important cost and labor savings.

Embodiments of the present invention include unique combinations of strong mineral acids and weak organic acids or salts thereof which solve the problem of maintaining the pH of the foot bath at a predetermined level (e.g., below pH 4.5) during the useful life of the foot bath. Embodiments of these concentrate compositions are capable of maintaining a pH in a range of about 2.0 to about 4.5 by introducing a single dose of one or more weak organic acid or salts thereof at the start of the bath with no necessity to add additional acid. The concentration of weak organic acids or salts thereof should be in the range of about 1.0% (wt/wt) to about 20% (wt/wt) of the overall solution (e.g., any value or range of values therein), although other concentrations may also be effectively used. In some examples, the one or more weak organic acids may be present in a concentration in the range of about 1% wt/wt to about 10% wt/wt. In other examples, the one or more weak acids may be present in a concentration from about 1% wt/wt to about 5% wt/wt. It is preferred to provide a ratio of about 4 parts metal salt to about 1-2 parts weak organic acid or salts thereof, although other ratios may also be effectively used.

Embodiments of the present invention include unique combinations of strong mineral acids and one or more polyprotic organic acids or salts thereof which solve the problem of maintaining the pH of the foot bath at a predetermined level (e.g., below pH 4.5) during the useful life of the foot bath. Embodiments of these concentrate compositions are capable of maintaining a pH in a range of about 2.0 to about 4.5 by introducing a single dose of one or more polyprotic organic acids or salts thereof at the start of the bath with no necessity to subsequently add additional acid. The concentration of the one or more polyprotic organic acids or salts thereof should be in the range of about 1.0% (wt/wt) to about 15.0% (wt/wt) of the overall solution (e.g., any value or range of values therein), although other concentrations may also be effectively used. In some examples, the one or more strong acids may be present in a concentration in the range of about 1% wt/wt to about 10% wt/wt. In other examples, the one or more strong acids may be present in a concentration from about 1% wt/wt to about 5% wt/wt. It is preferred to provide a ratio of about 4 parts metal salt to about 1-1.5 parts polyprotic organic acid(s) or salts thereof, although other ratios may also be effectively used.

Embodiments of the present invention include unique combinations of strong mineral acids and one or more diprotic organic acids or salts thereof which solve the problem of maintaining the pH of the foot bath at a predetermined level (e.g., below pH 4.5) during the useful life of the foot bath. Embodiments of these concentrate compositions are capable of maintaining a pH in a range of about 2.0 to about 4.5 by introducing a single dose of one or more diprotic organic acids or salts thereof at the start of the bath with no necessity to subsequently add additional acid. The concentration of the one or more diprotic organic acids or salts thereof should be in the range of about 1.0% (wt/wt) to about 10.0% (wt/wt) of the overall solution (e.g., any value or range of values therein), although other concentrations may also be effectively used. In some examples, the one or more diprotic organic acids or salts thereof may be present in a concentration in the range of about 1% wt/wt to about 10% wt/wt. In other examples, the one or more diprotic organic acids or salts thereof may be present in a concentration from about 1% wt/wt to about 5% wt/wt. It is preferred to provide a ratio of about 4 parts metal salt to about 1-1.5 parts diprotic organic acid(s) or salts thereof, although other ratios may also be effectively used.

Embodiments of the present invention include unique combinations of strong mineral acids and one or more triprotic organic acids or salts thereof which solve the problem of maintaining the pH of the foot bath at a predetermined level (e.g., below pH 4.5) during the useful life of the foot bath. Embodiments of these concentrate compositions are capable of maintaining a pH in a range of about 2.0 to about 4.5 by introducing a single dose of one or more triprotic organic acids or salts thereof at the start of the bath with no necessity to subsequently add additional acid. The concentration of the one or more triprotic organic acids or salts thereof should be in the range of about 1.0% (wt/wt) to about 10.0% (wt/wt) of the overall solution (e.g., any value or range of values therein), although other concentrations may also be effectively used. In some examples, the one or more triprotic organic acids or salts thereof may be present in a concentration in the range of about 1% wt/wt to about 7.5% wt/wt. In other examples, the one or more triprotic organic acids or salts thereof may be present in a concentration from about 1% wt/wt to about 5% wt/wt. It is preferred to provide a ratio of about 4 parts metal salt to about 1-1.5 parts triprotic organic acid(s) or salts thereof, although other ratios may also be effectively used.

Embodiments of the present invention include unique combinations of strong mineral acids, citric acid and optionally one or more additional weak organic acids which solve the problem of maintaining the pH of the foot bath at a very low level during the useful life of the foot bath. Embodiments of these concentrate compositions are capable of maintaining a pH in a range of about 2.0 to about 4.5 by introducing a single dose of citric acid and optionally one or more additional weak inorganic acids at the start of the bath with no necessity to subsequently add additional acid. In examples that include a combination of citric acid and/or a salt thereof, with one or more other weak organic acids and/or salts thereof, the concentration of the combination of citric acid in a range of about 1.0% (wt/wt) to about 10.0% (wt/wt) of the overall solution (e.g., any value or range of values therein). In some examples, a combination of citric acid and/or a salt thereof, with one or more other weak organic acids and/or salts thereof may be present in a concentration in the range of about 1% wt/wt to about 7.5% wt/wt. In other examples, a combination of citric acid and/or a salt thereof, with one or more other weak organic acids and/or salts thereof may be present in a concentration from about 1% wt/wt to about 5% wt/wt. In examples that include citric acid and/or salts thereof as a weak organic acid, the concentration of citric acid and/or salts thereof should be in the range of about 3.5% (wt/wt) to about 7.5% (wt/wt) (e.g., about 5% [wt/wt]) of the overall solution, although other concentrations may also be effectively used. It is preferred to provide a ratio of about 4 parts metal salt to about 1 part citric acid, although other ratios may also be effectively used.

Embodiments of the present include unique combinations of strong mineral acids and one or more polyprotic organic acids or salts thereof in a final footbath solution which solve the problem of maintaining the pH of the foot bath at a predetermined level (e.g., below pH 4.5) during the useful life of the foot bath. Embodiments of these final footbath compositions are capable of maintaining a pH in a range of about 2.0 to about 4.5. The composition may be a final footbath solution that includes one or more copper or zinc compounds in a range of about 0.5% to about 1.25% (w/w) (e.g., about 0.75% to about 1% [w/w]). The one or more weak organic acids may be present in the diluted footbath solution in a range of about 0.1% (w/w) to about 0.5% (w/w)

(e.g., about 0.15% [w/w] to about 0.3% [w/w] or any value therein). The one or more strong inorganic acids may be present in the aqueous solution in a range of about 0.05% (w/w) to about 0.5% (w/w) (e.g., about 0.1% [w/w] to about 0.3% [w/w] or any value therein). For example, the strong inorganic acid may be sulfuric acid in a concentration of between about 0.1% and about 0.5% wt/wt in the concentrate solution. The final foot bath solution may provide a solution that maintains pH at or below 4.5 after being used to wash and treat up to about 500 cattle or other livestock.

In some aspects, the present invention relates to a composition for use in a livestock foot bath which helps maintain the solubility of dissolved metal ions comprising an aqueous solution containing at least one of a copper salt and a zinc salt; a strong inorganic acid; and at least one organic polyprotic acid in an amount sufficient to inhibit copper and zinc ions from precipitating out of said composition when said composition is fouled by organic waste in said livestock foot bath. The at least one of a copper salt and a zinc salt may be present in an amount of about 1% wt/wt to about 35% wt/wt. The at least one of a copper salt and a zinc salt may be present in an amount of about 1% wt/wt to about 25% wt/wt. The at least one of a copper salt or a zinc salt may be provided in a concentration of between about 5% wt/wt and about 35% wt/wt. The at least one of a copper salt or a zinc salt may be provided in a concentration of between about 5% wt/wt and about 20% wt/wt. The copper salt may be present in an amount of about 1% wt/wt to about 15% wt/wt. The copper salt may be present in an amount of about 1% wt/wt to about 10% wt/wt. The zinc salt may be present in an amount of about 1% wt/wt to about 15% wt/wt. The zinc salt may be present in an amount of about 1% wt/wt to about 10% wt/wt. The copper salt may be a copper sulfate compound. The zinc salt may be a zinc sulfate compound. The at least one organic polyprotic acid may be provided in a concentration of between about 1% wt/wt to about 10% wt/wt. The at least one organic polyprotic acid may be provided in a concentration of between about 3% and about 8% wt/wt in said aqueous solution. The at least one organic polyprotic acid may be provided in a concentration of between about 4% and about 6% wt/wt in said aqueous solution. The at least one organic polyprotic acid may be provided in a concentration of between about 1% wt/wt to about 5% wt/wt. The at least one organic polyprotic acid may be provided in a concentration of up to about 5% wt/wt. The at least one organic polyprotic acid may be provided in a concentration of between about 4% and about 6% wt/wt in said aqueous solution. The at least one organic polyprotic acid may comprise citric acid. The citric acid may be provided in a concentration in a range of about 1% wt/wt to about 5% wt/wt in said aqueous solution. The strong inorganic acid may be present in a range of about in an amount from about 1% wt/wt to about 10% wt/wt in said aqueous solution. The strong inorganic acid may be present in a range of about in an amount from about 1% wt/wt to about 5% wt/wt in said aqueous solution. The strong inorganic acid may be present in a range of about in an amount up to about 5% wt/wt in said aqueous solution. The strong inorganic acid may be present in a range of about in an amount from about 2.5% wt/wt to about 4% wt/wt in said aqueous solution. The strong inorganic acid may be provided in a concentration of about 2.5 to about 3.5% wt/wt in said aqueous solution. The strong inorganic acid may be provided in a concentration of about 3.3% wt/wt in said aqueous solution. The strong inorganic acid may comprise sulfuric acid. A dilution of said aqueous solution for use in a cattle foot bath may comprise said at least one organic polyprotic acid in a concentration of between about 0.1% wt/wt and about 0.5% wt/wt. A dilution of said aqueous solution for use in a cattle foot bath may comprise said at least one organic polyprotic acid in a concentration of between about 0.2% wt/wt and about 0.4% wt/wt. A dilution of said aqueous solution for use in a cattle foot bath may comprise said strong inorganic acid in a concentration from about 0.1% wt/wt to about 0.5% wt/wt. A dilution of said aqueous solution for use in a cattle foot bath may comprise said strong inorganic acid in a concentration from about 0.125% wt/wt to about 0.4% wt/wt. The aqueous solution may be non-colloidal and has low viscosity.

In another aspect, a method for increasing the useful life of a livestock foot bath by inhibiting the precipitation of metal salts therein comprising the steps of preparing an aqueous solution for said foot bath including at least one of a copper sulfate compound or a zinc sulfate compound; a strong inorganic acid; and at least one polyprotic organic acid in a sufficient amount to inhibit copper and zinc ions from precipitating out of said composition when said composition is fouled by organic waste in said livestock foot bath. The aqueous solution may be non-colloidal and has low viscosity. The strong inorganic acid may comprise sulfuric acid. The copper sulfate compound may be selected from the group consisting of $CuSO_4$, $CuSO_4(H_2O)$, $CuSO_4(H_2O)_2$, $CuSO_4(H_2O)_3$, $CuSO_4(H_2O)_4$, $CuSO_4(H_2O)_5$, and combinations thereof. The zinc sulfate compound may be selected from the group consisting of $ZnSO_4$, $ZnSO_4(H_2O)$, $ZnSO_4(H_2O)_6$, $ZnSO_4(H_2O)_7$, and combinations thereof. The at least one of a copper salt and a zinc salt may be present in an amount of about 1% wt/wt to about 35% wt/wt. The at least one of a copper salt and a zinc salt may be present in an amount of about 1% wt/wt to about 25% wt/wt. The at least one of a copper salt or a zinc salt may be provided in a concentration of between about 5% wt/wt and about 35% wt/wt. The at least one of a copper salt or a zinc salt may be provided in a concentration of between about 5% wt/wt and about 20% wt/wt. The copper salt may be present in an amount of about 1% wt/wt to about 15% wt/wt. The copper salt may be present in an amount of about 1% wt/wt to about 10% wt/wt. The zinc salt may be present in an amount of about 1% wt/wt to about 15% wt/wt. The zinc salt may be present in an amount of about 1% wt/wt to about 10% wt/wt. The copper salt may be a copper sulfate compound. The zinc salt may be a zinc sulfate compound. The at least one organic polyprotic acid may be provided in a concentration of between about 1% wt/wt to about 10% wt/wt. The at least one organic polyprotic acid may be provided in a concentration of between about 3% and about 8% wt/wt in said aqueous solution. The at least one organic polyprotic acid may be provided in a concentration of between about 4% and about 6% wt/wt in said aqueous solution. The at least one organic polyprotic acid may be provided in a concentration of between about 1% wt/wt to about 5% wt/wt. The at least one organic polyprotic acid may be provided in a concentration of up to about 5% wt/wt. The at least one organic polyprotic acid may be provided in a concentration of between about 4% and about 6% wt/wt in said aqueous solution. The at least one organic polyprotic acid may comprise citric acid. The citric acid may be provided in a concentration in a range of about 1% wt/wt to about 5% wt/wt in said aqueous solution. The strong inorganic acid may be present in a range of about in an amount from about 1% wt/wt to about 10% wt/wt in said aqueous solution. The strong inorganic acid may be present in a range of about in an amount from about 1% wt/wt to about 5% wt/wt in said aqueous solution. The strong inorganic acid may be present in a range of about in an amount up to about 5% wt/wt in said aqueous solution. The strong inorganic acid may be present in a range of about in an amount from about 2.5% wt/wt to about 4% wt/wt in said aqueous solution. The strong inorganic acid may be provided in a concentration of about 2.5 to about 3.5% wt/wt in said aqueous solution. The strong inorganic acid may be provided in a concentration of about 3.3% wt/wt in said aqueous solution.

In a further aspect, the invention relates to a composition for use in a livestock foot bath which helps maintain the solubility of dissolved metal ions comprising an aqueous solution including at least one of a copper salt or a zinc salt; and at least one organic polyprotic acid in a concentration sufficient to inhibit copper and zinc ions from precipitating out of said composition when said composition is fouled by organic waste in said livestock foot bath. The composition may further include an inorganic acid in concentration of up to about 10.0%. The inorganic acid may be a strong acid. The inorganic acid may comprise sulfuric acid. The copper salt may be a copper sulfate compound. The zinc salt may be a zinc sulfate compound. The weight ratio of the at least one of a copper salt or a zinc salt to the strong inorganic acid may be in a range of about 1:1 to about 10:1 The weight ratio of the at least one of a copper salt or a zinc salt to the strong inorganic acid may be in a range of about 5:2 to about 10:1. The weight ratio of the at least one of a copper salt or a zinc salt to the at least one organic polyprotic acid may be in a range of about 1:1 to about 10:1. The weight ratio of the at least one of a copper salt or a zinc salt to the at least one organic polyprotic acid may be in a range of about 1:1 to about 8:1. The weight ratio of the strong inorganic acid to the at least one organic polyprotic acid may be in a range of about 1.1 to about 1:10. The weight ratio of the strong inorganic acid to the at least one organic polyprotic acid may be in a range of about 4:3 to about 1:10. The weight ratio of the strong inorganic acid to the at least one organic polyprotic acid may be in a range of about 1:1 to about 1:3. The at least one organic polyprotic acid may comprise citric acid. The aqueous solution may be non-colloidal and have low viscosity.

It is therefore an object of the present invention to provide improved livestock foot bath solutions that provide effective treatment of livestock hooves for long periods of time.

It is also an object of the present invention to provide improved livestock foot bath solutions that can treat up to 500 cows before needing to be changed, replaced or amended.

It is also an object of the present invention to provide improved livestock foot bath solutions containing aqueous solutions of metal salts together with one or more weak organic acids or salts thereof in which the metal salts stay in solution for long periods of time during use.

It is also an object of the present invention to provide improved livestock foot bath solutions containing aqueous solutions of metal salts together with one or more polyprotic organic acids or salts thereof in which the metal salts stay in solution for long periods of time during use.

It is also an object of the present invention to provide improved livestock foot bath solutions containing aqueous solutions of metal salts together with citric acid and/or salts thereof in which the metal salts stay in solution for long periods of time during use.

It is also an object of the present invention to provide improved livestock foot bath solutions containing aqueous solutions of metal salts together with one or more weak organic acid and/or salts thereof and a strong acid in which the metal salts stay in solution for long periods of time during use.

It is also an object of the present invention to provide improved livestock foot bath solutions containing aqueous solutions of metal salts together with one or more polyprotic organic acids or salts thereof and a strong acid in which the metal salts stay in solution for long periods of time during use.

It is also an object of the present invention to provide improved livestock foot bath solutions containing aqueous solutions of metal salts together with citric acid and/or salts thereof and a strong acid in which the metal salts stay in solution for long periods of time during use.

It is further object of the invention to provide improved livestock foot bath solutions containing aqueous solutions of copper or zinc salts together with citric acid which are capable of treating up to 500 cows before needing to be changed, replaced or amended.

It is further object of the invention to provide methods of treating livestock hooves using footbaths containing improved compositions containing aqueous solutions of metal salts together with a weak organic acid.

It is further object of the invention to provide methods of treating livestock hooves using footbaths containing improved compositions containing aqueous solutions of metal salts together with a weak organic acid and a strong inorganic acid.

It is further object of the invention to provide methods of treating livestock hooves using footbaths containing improved compositions containing aqueous solutions of copper or zinc salts together with citric acid.

It is further object of the invention to provide methods of treating livestock hooves using footbaths containing improved compositions containing aqueous solutions of copper or zinc salts together with citric acid and sulfuric acid.

Additional objects of the invention will be apparent from the detailed descriptions and the claims herein.

DETAILED DESCRIPTION

Figure 1:
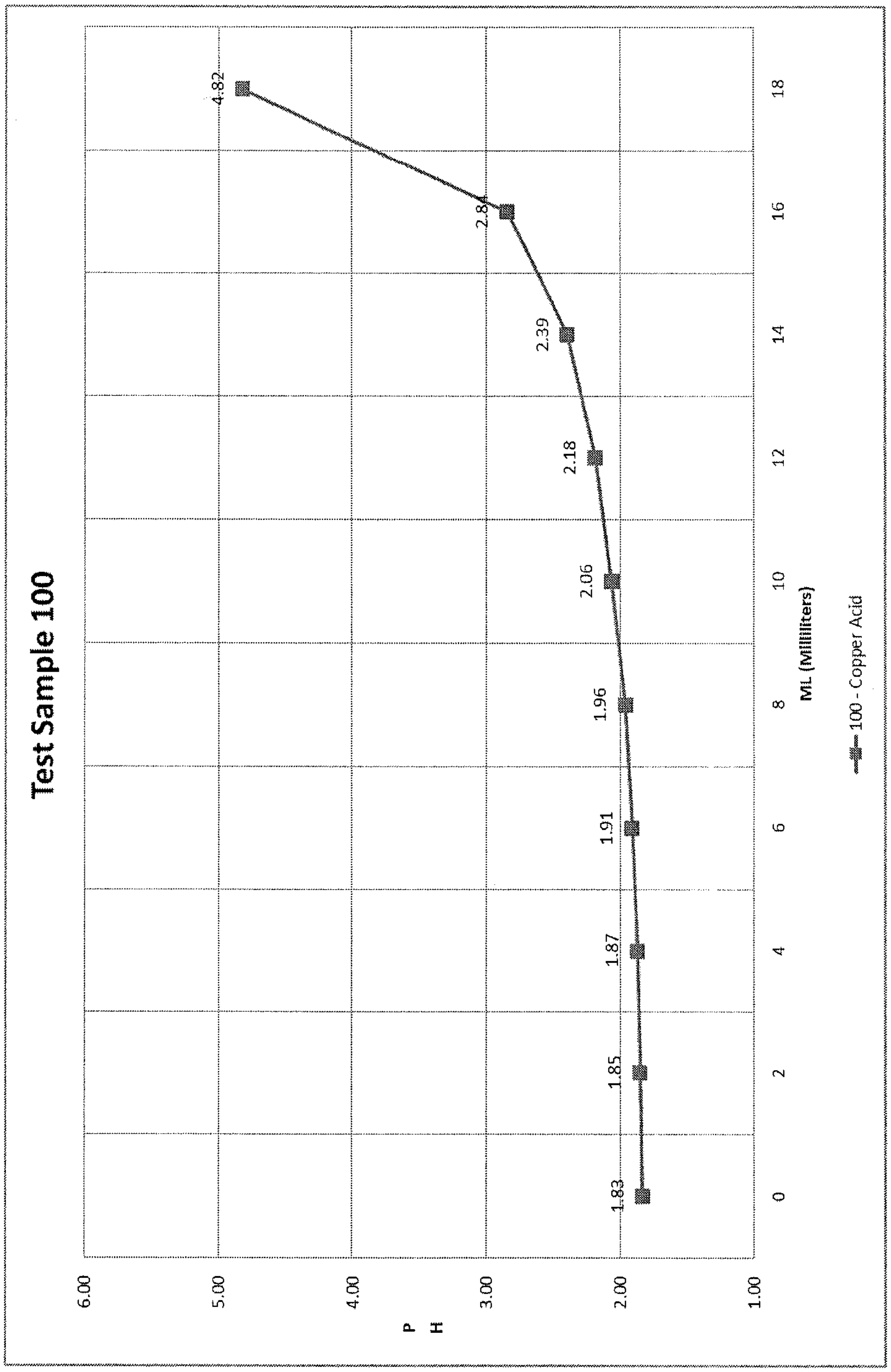
FIG. 1 is a graph of an exemplary pH titration curve (100) for a copper mixture.

Referring to the drawings and to the examples and tables below, it is to be understood that the titration of the acids in dairy foot bath compositions with ammonium hydroxide simulates the neutralizing effect of alkaline compounds in the animal waste deposited in actual foot bath water. The total amount of ammonium hydroxide needed to bring a sample of a composition to pH above 5.0 is an accurate indication of its effectiveness in maintaining the bath pH a low level.

The compositions of the present invention may include a concentrated aqueous solution of one or more zinc or copper compounds (e.g., copper sulfate or salt thereof, zinc sulfate or salt thereof), one or more strong inorganic acids (e.g., $H_2SO_4$, HCl, $H_2NO_3$, or $H_3PO_4$), and one or more weak organic acids or salts thereof. The one or more copper or zinc compounds or salts may be present in the aqueous solution in a range of about 1% (w/w) to about 35% (w/w) (e.g., about 5% [w/w] to about 35% [w/w]; about 1% [w/w] to about 25% [w/w]; or any value or range of values therein). The one or more weak organic acids may be present in the aqueous solution in a range of about 1% (w/w) to about 10% (w/w) (e.g., about 1% [w/w] to about 5% [w/w]; about 4% [w/w] to about 6% [w/w]; or any value or range of values therein). The one or more strong inorganic acids may be present in the aqueous solution in a range of about 1% (w/w) to about 4% (w/w) (e.g., about 2.5% [w/w] to about 3.5% [w/w] or any value therein). For example, the strong inorganic acid may be sulfuric acid in a concentration of between about 2.5% and about 3.5% wt/wt in the concentrate solution.

The copper or zinc compound may be $CuSO_4$, $CuSO_4(H_2O)$, $CuSO_4(H_2O)_2$, $CuSO_4(H_2O)_3$, $CuSO_4(H_2O)_4$, $CuSO_4(H_2O)_5$, $ZnSO_4$, $ZnSO_4(H_2O)$, $ZnSO_4(H_2O)_6$, $ZnSO_4(H_2O)_7$, and combinations thereof.

The one or more weak organic acids may include citric acid, succinic acid, 2,3 dihydroxylated succinic acid, glutaric acid, hexanedioic acid, heptanedioic acid, octanedioic acid, nonanedioic acid, decanedioic acid, malic acid, fumaric acid, aconitic acid, Isocitric acid, Propane-1,2,3-tricarboxylic acid, benzene-1,3,5-tricarboxylic acid, benzene-1,3,5-tricarboxylic acid, salts of such organic acids, and combinations thereof.

The final foot bath solution may be prepared by combining the concentrate solution with water in a ratio in a range of 1:1 to 1:30 (concentrate:water) prior to being placed in a livestock footbath. For example, the concentrate solution may be diluted in water to a 5% diluted solution. 5% diluted solution may then be added to a livestock footbath for cleaning hooves or feet. The final footbath solution may be agitated to disperse the concentrate solution into diluted mixture. The final footbath solution may be agitated by a Venturi tube such that the agitation may occur efficiently within a conduit system for delivering the final footbath solution into the livestock footbath. Other agitation methods of agitation are also within the scope of the present invention, such as mixing the solution manual or with a motorized stirring rod in a bath prior to addition to the livestock footbath.

After the dilution step, the diluted footbath solution of the present invention may include one or more copper or zinc compounds in a range of about 0.1% to about 3.5% (w/w) (e.g., about 0.5% [w/w] to about 2.5% [w/w]; about 0.75% [w/w] to about 1.5% [w/w]; or any value or range of values therein). The one or more weak organic acids may be present in the diluted footbath solution in a range of about 0.1% (w/w) to about 1.0% (w/w) (e.g., about 0.1% [w/w] to about 0.5% [w/w]; about 0.2% [w/w] to about 0.4% [w/w]; about 0.3% [w/w] to about 0.35% [w/w]; or any value or range of values therein). The one or more strong inorganic acids may be present in the aqueous solution in a range of about 0.1% (w/w) to about 0.10% (w/w) (e.g., about 0.2% [w/w] to about 0.8% [w/w]; about 0.1% [w/w] to about 0.5% [w/w]; about 0.125% [w/w] and about 0.175% [w/w]; or any value or range of values therein). For example, the strong inorganic acid may be sulfuric acid in a concentration of between about 0.125% and about 0.175% wt/wt in the concentrate solution. The final foot bath solution may provide a solution that maintains pH at or below 4.5 after being used to wash and treat up to about 500 cattle or other livestock.

The following examples and tables display titration curves which will show the effectiveness of embodiments of the present invention resulting from laboratory experiments. All chemicals were titrated at concentrations found in foot baths. In each example, the compositions were diluted to 5% w/w in 400 gm of water. The neutralizing capacity of each solution was determined by titrating with a 1.25% ammonium hydroxide solution, which simulates the alkali waste produced by livestock. The endpoint for the titration was determined to be the pH at which a stable precipitate of metals formed, i.e. approaching or reaching 5.0. The total number of millimeters of ammonium hydroxide to reach that pH value is given as the titer in millimeters.

Example 1A

This exemplary example (Test Sample 100 as shown in FIG. 1) used a solution of copper sulfate pentahydrate, sulfuric acid and water without any citric acid or other weak organic acid. In contrast, example 1B below used the same components plus citric acid. In particular, this example solution contained a mixture of 100 gm of $CuSO_{4.5}H_2O$, 15 gm of $H_2SO_4$ and 385 gm of $H_2O$. A 5% w/w solution, which is similar to a dairy foot bath concentration, was prepared by mixing 20 gm of the composition with 380 gm $H_2O$ and then titrating it with doses of 2 ml ammonium hydroxide 1.25% solution to the end point shown in Table 1 below.

Example 1B

Figure 2:
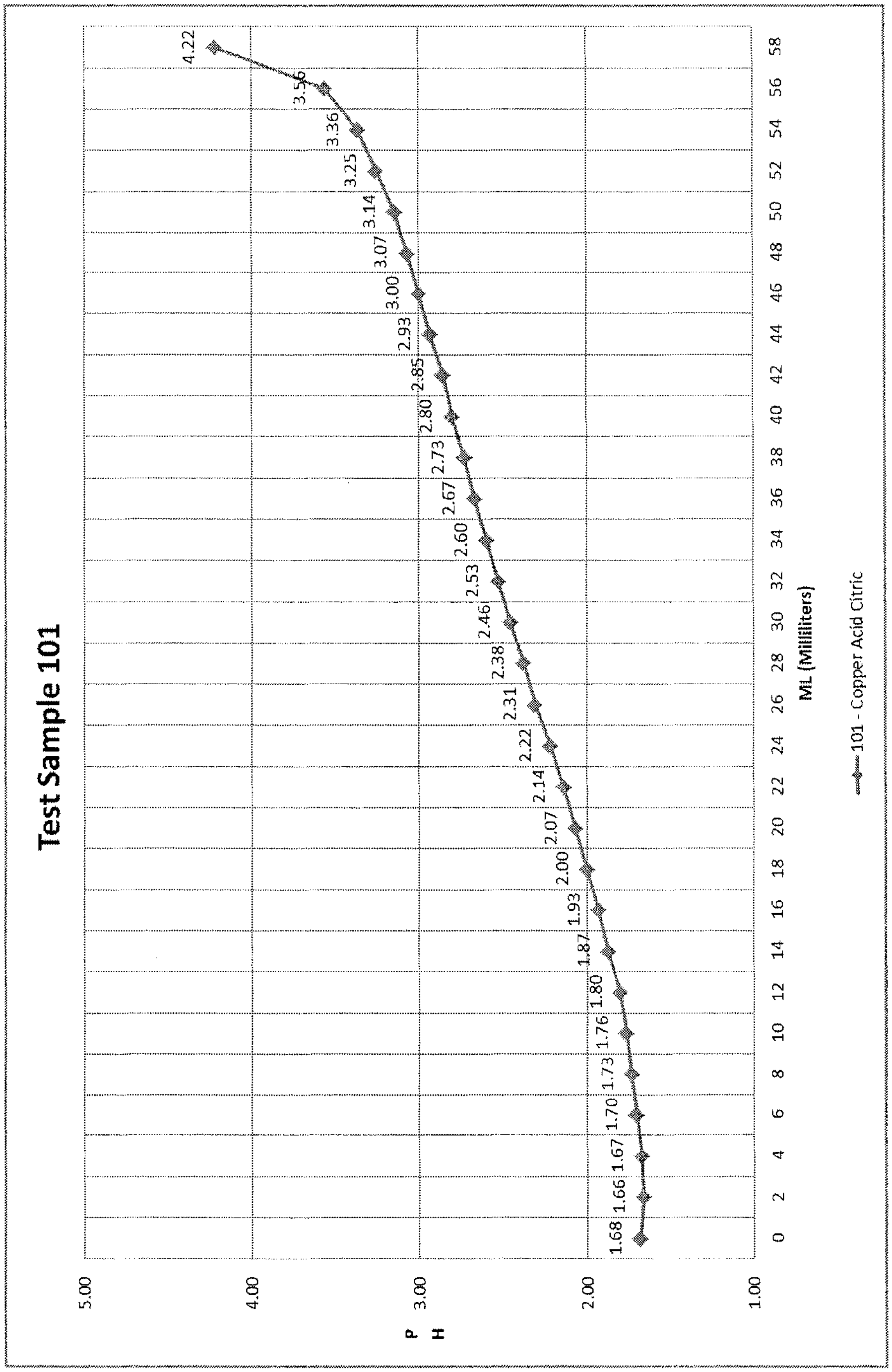
FIG. 2 is a graph of an exemplary pH titration curve (101) for a copper and citric acid mixture.

This exemplary example (Test Sample 101 as shown in FIG. 2) used a solution of copper sulfate pentahydrate, sulfuric acid, citric acid and water. In particular, this example solution contained a mixture of 100 gm $CuSO_{4.5}H_2O$, 15 gm $H_2SO_4$, 25 gm citric acid and 360 gm $H_2O$. A 5% w/w solution, which is similar to a dairy foot bath concentration, was prepared by mixing 20 gm of the composition with 380 gm $H_2O$ and titrating to the end point shown in Table 1 below.

As shown in Table 1 below, it can be seen that the solution of example 1A reached a pH of 5 after only 20 ml of ammonium hydroxide solution, whereas the solution of example 1B (which also contained citric acid) did not reach pH 5 until 64 ml of ammonium hydroxide was added.

TABLE 1

| TEST SAMPLE | ENDPOINT | TITER |
|---|---|---|
| Test Sample 100 | pH 5.1 | 20 ml. |
| Test Sample 101 | pH 5.2 | 64 ml. |

Example 2A

Figure 3:
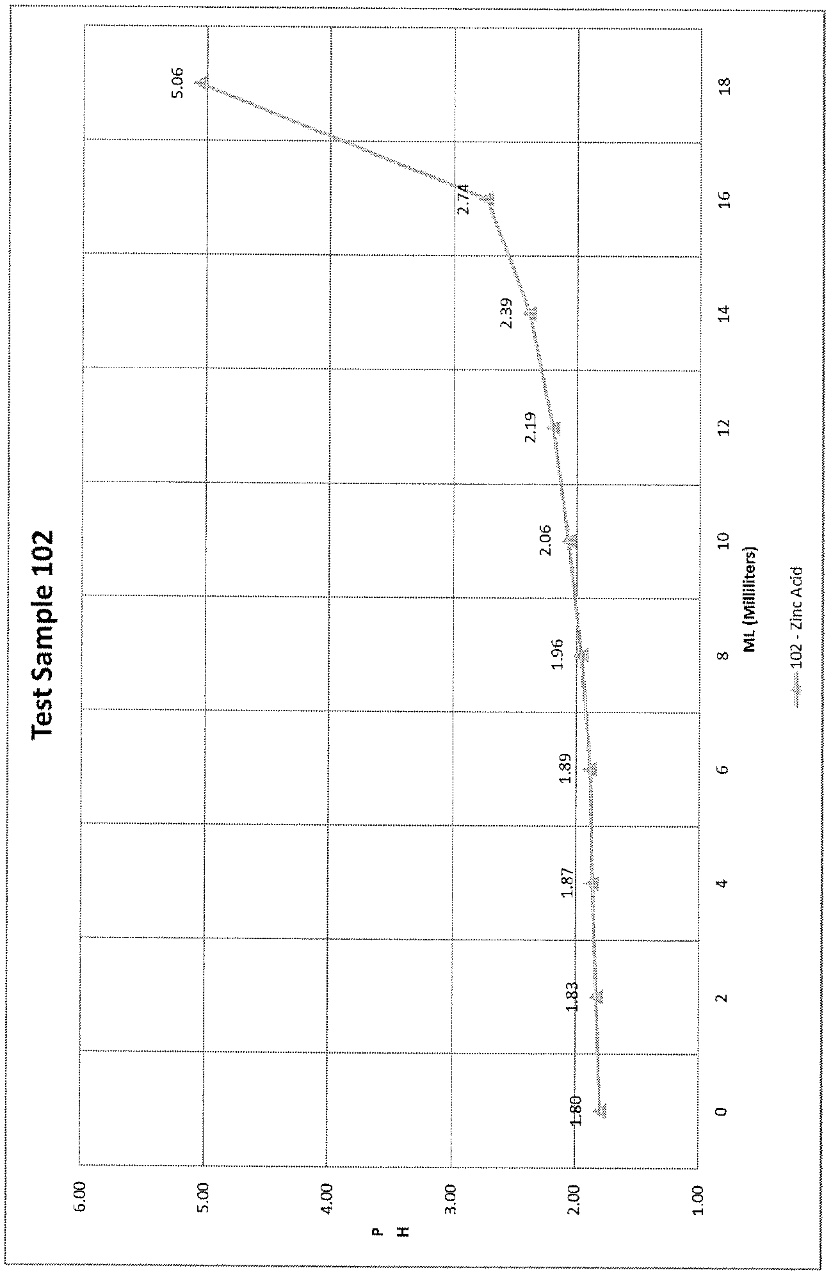
FIG. 3 is a graph of an exemplary pH titration curve (102) for a zinc mixture.

This exemplary example (Test Sample 102 as shown in FIG. 3) used a solution of zinc sulfate monohydrate, sulfuric acid and water without any citric acid or other weak organic acid. In contrast, example 2B below used the same components plus citric acid. In particular, this example solution contained a mixture of 100 gm $ZnSO_4{\cdot}H_2O$, 15 gm $H_2SO_4$ and 385 gm $H_2O$ were mixed. A 5% w/w solution, which is similar to dairy foot bath concentration, was prepared by mixing 20 gm of the composition with 380 gm $H_2O$ and then titrating it to the endpoint specified in Table 2 below.

Example 2B

Figure 4:
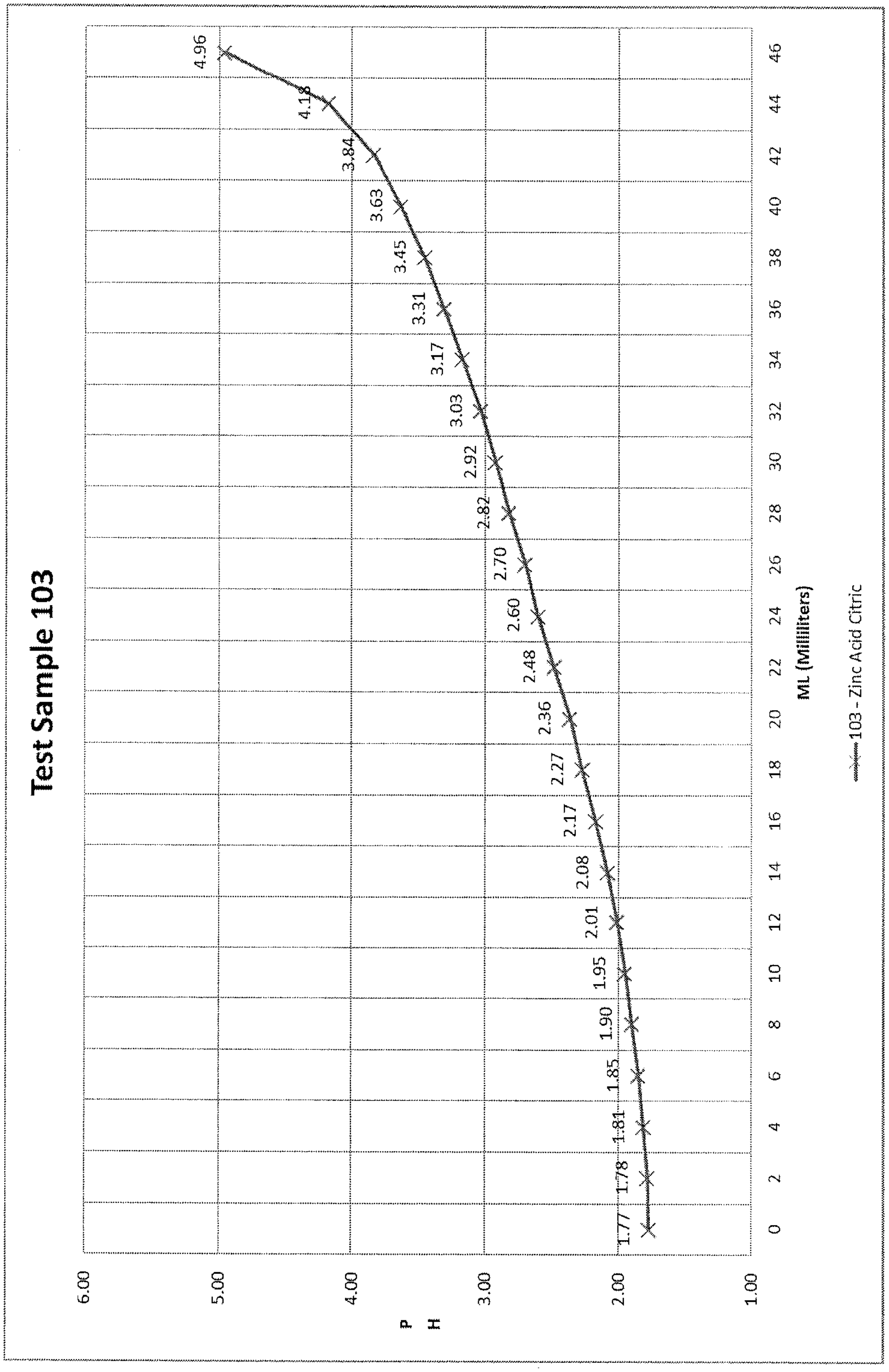
FIG. 4 is a graph of an exemplary pH titration curve (103) for a zinc and citric acid mixture.

This exemplary example (Test Sample 103 as shown in FIG. 4) used a solution of zinc sulfate monohydrate, sulfuric acid, citric acid and water. In particular, this example solution contained a mixture of 100 gm $ZnSO_4{\cdot}H_2O$, 15 gm $H_2SO_4$, 25 gm citric acid and 360 gm water were mixed. A 5% w/w solution, similar to the concentration in dairy foot baths, was prepared and titrated to the endpoint shown in Table 2 below.

As shown in Table 2 below, it can be seen that the solution of example 2A reached a pH of 5 after only 18 ml of ammonium hydroxide solution, whereas the solution of example 2B (which also contained citric acid) did not reach pH 5 until over 46 ml of ammonium hydroxide was added.

TABLE 2

| TEST SAMPLE | ENDPOINT | TITER |
|---|---|---|
| Test Sample 102 | pH 5.1 | 18 ml. |
| Test Sample 103 | pH 4.96 | 46 ml. |

Example 3A

Figure 5:
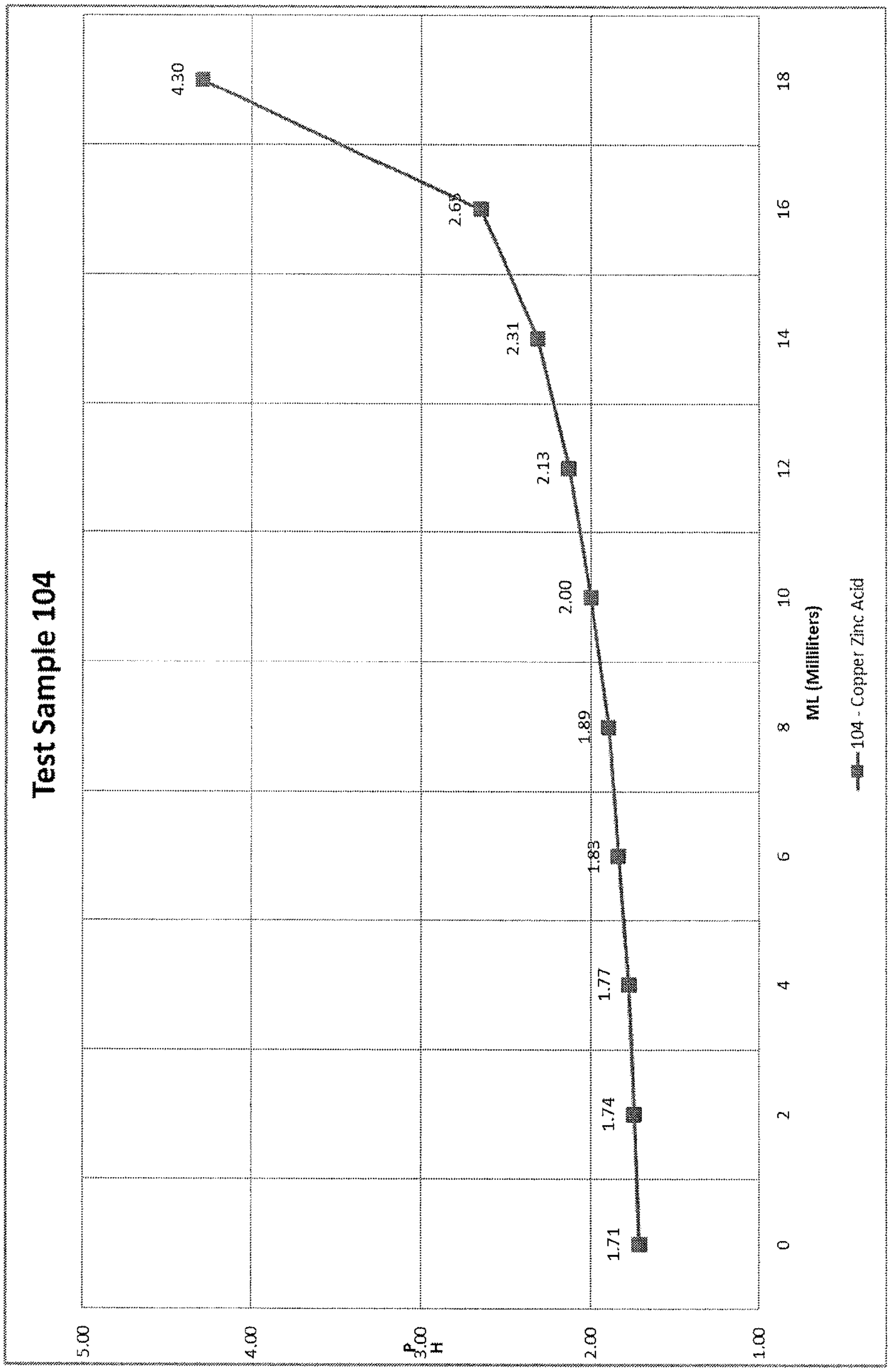
FIG. 5 is a graph of an exemplary pH titration curve (104) for copper and zinc mixture.

This exemplary example (Test Sample 104 as shown in FIG. 5) used a solution of copper sulfate pentahydrate, zinc sulfate monohydrate, sulfuric acid and water without any citric acid or other weak organic acid. In contrast, example 3B below used the same components plus citric acid. In particular, this example solution contained a mixture of 50 gm $CuSO_{4.5}H_2O$, 50 gm $ZnSO_4{\cdot}H_2O$, 15 gm $H_2SO_4$, and 385 gm $H_2O$. A 5% w/w solution, a similar concentration in foot baths, and titrated to the endpoint specified in Table 3 below.

Example 3B

Figure 6:
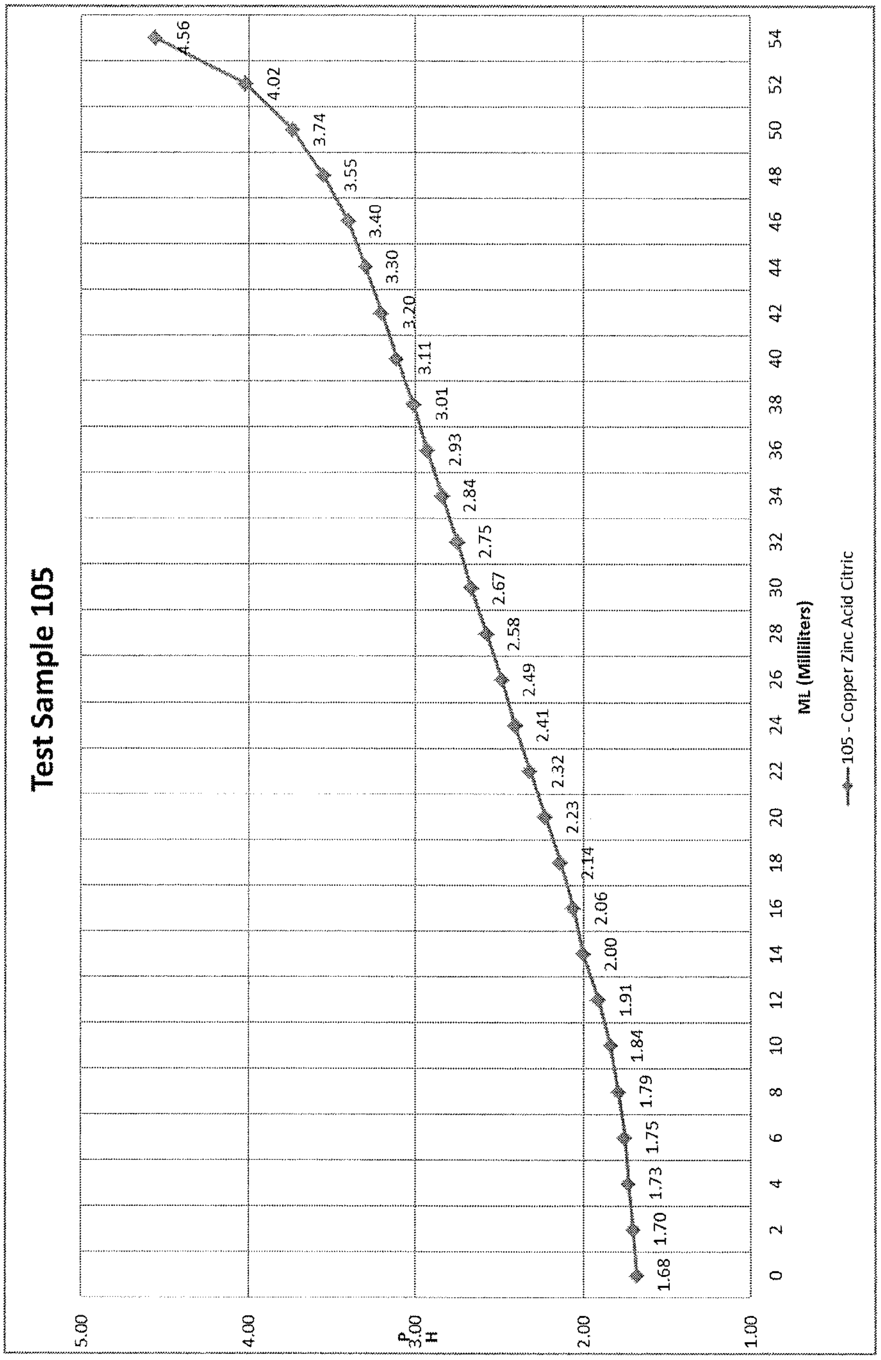
FIG. 6 is a graph of an exemplary pH titration curve (105) for copper, zinc and citric acid mixture.

This exemplary example (Test Sample 105 as shown in FIG. 6) used a solution of copper sulfate pentahydrate, zinc sulfate monohydrate, sulfuric acid, citric acid and water. In particular, this example solution contained a mixture of 50 gm $CuSO_4{\cdot}H_2O$, 50 gm $ZnSO_4{\cdot}H_2O$, 15 gm $H_2SO_4$, 25 gm Citric Acid, and 360 gm $H_2O$. A 5% w/w solution, a similar concentration in foot baths, and titrated to the endpoint specified in Table 3 below.

As shown in Table 3 below, it can be seen that the solution of example 3A reached a pH of 5 after only 20 ml of ammonium hydroxide solution, whereas the solution of example 3B (which also contained citric acid) did not reach pH 5 until over 54 ml of ammonium hydroxide was added.

TABLE 3

| TEST SAMPLE | ENDPOINT | TITER |
|---|---|---|
| Test Sample 104 | pH 5.25 | 20 ml. |
| Test Sample 105 | pH 4.56 | 54 ml. |

Figure 7:
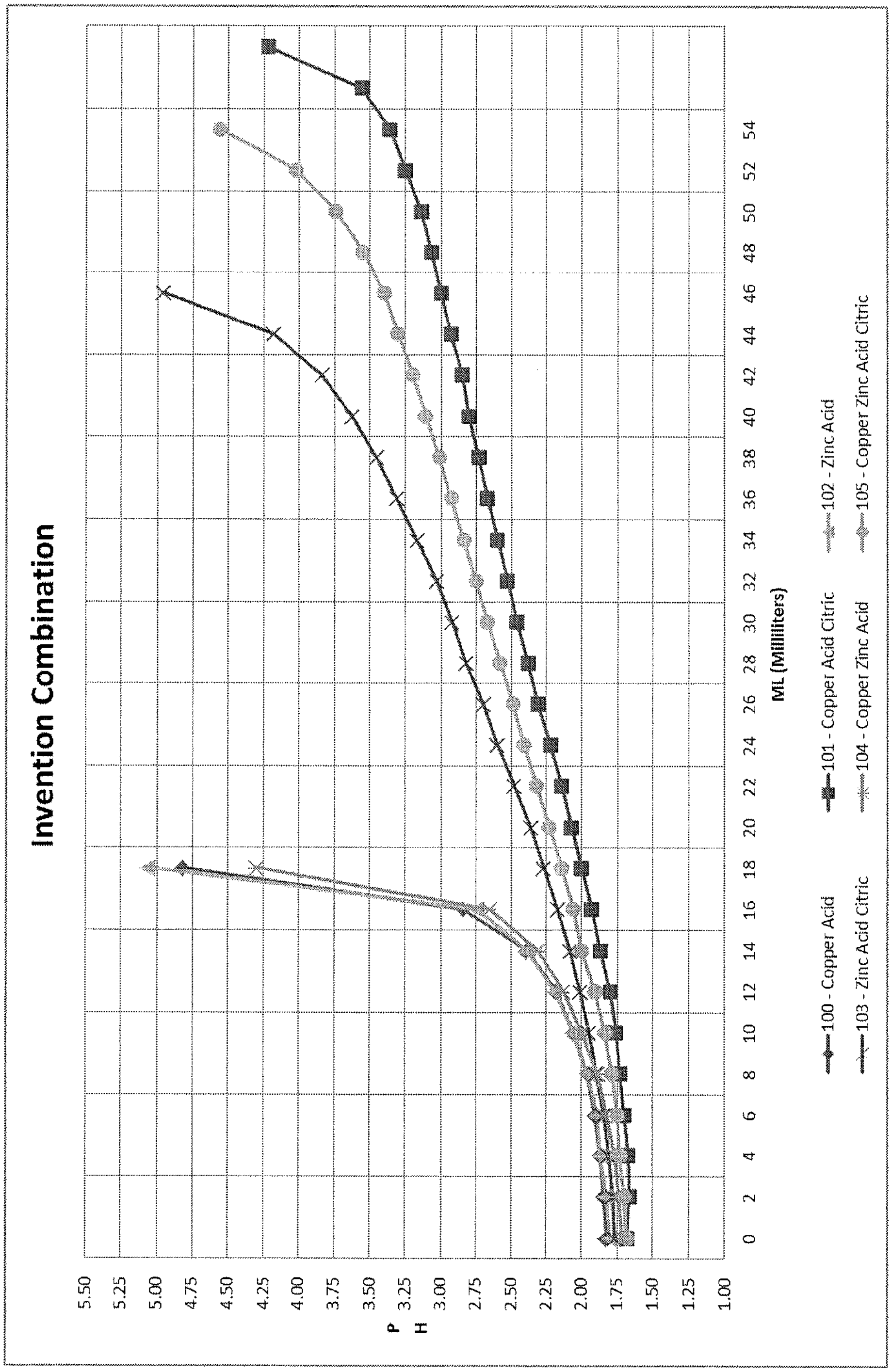
FIG. 7 is a combination graph showing each of the titration curves of FIGS. 1-6.
Figure 8:
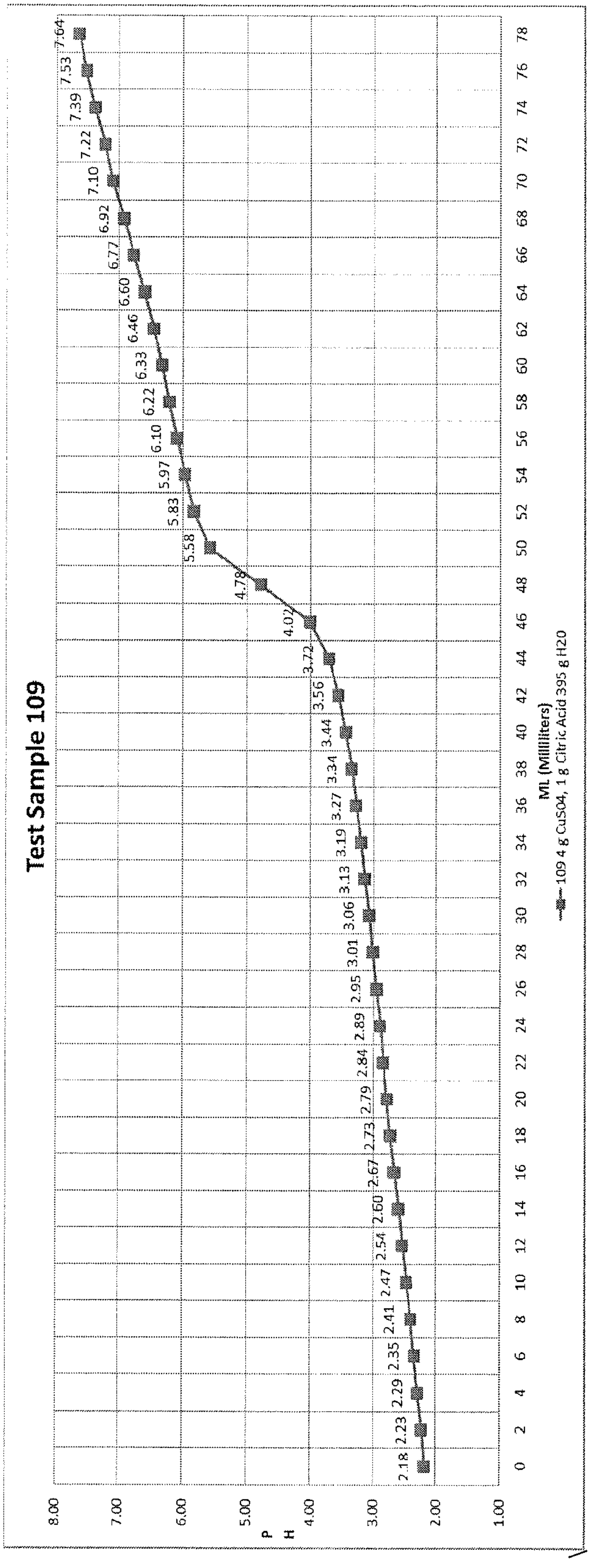
FIG. 8 is a graph of an exemplary pH titration curve (109) for a copper and citric acid mixture.
Figure 9:
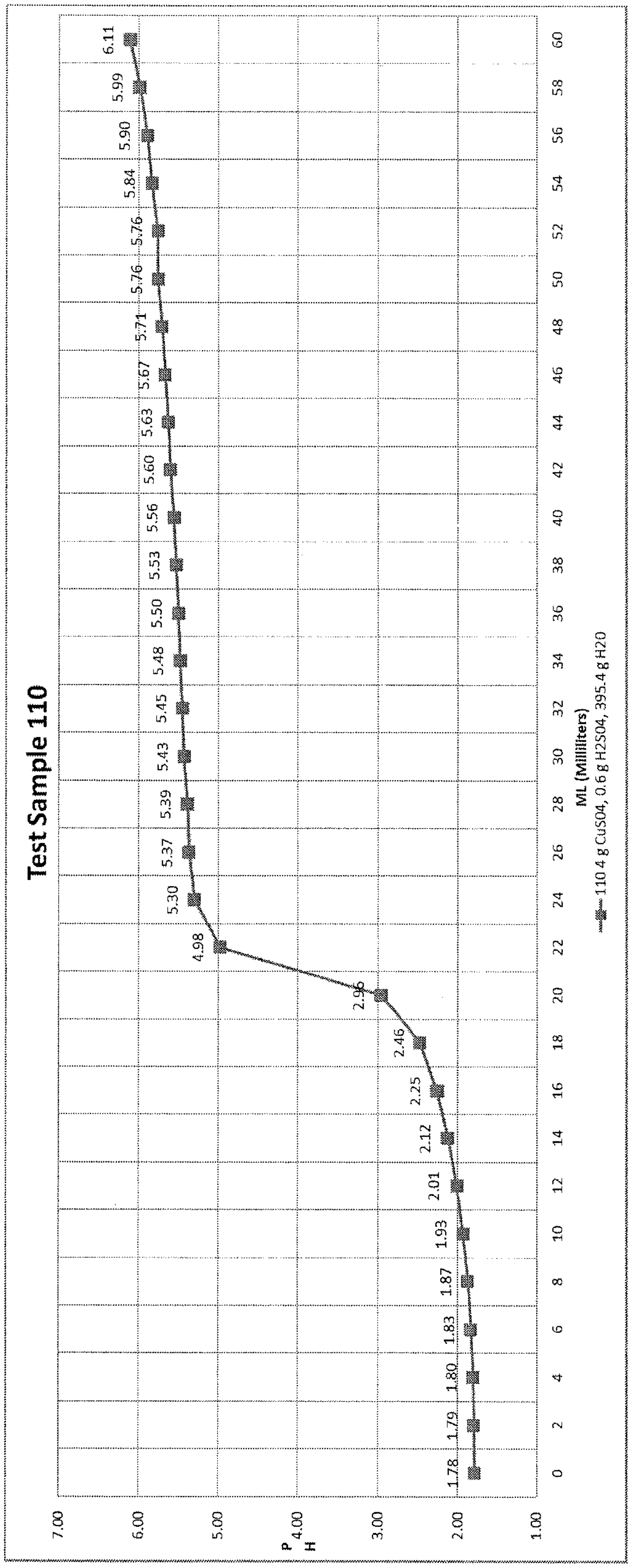
FIG. 9 is a graph of an exemplary pH titration curve (110) for a copper and sulfuric acid mixture.
Figure 10:
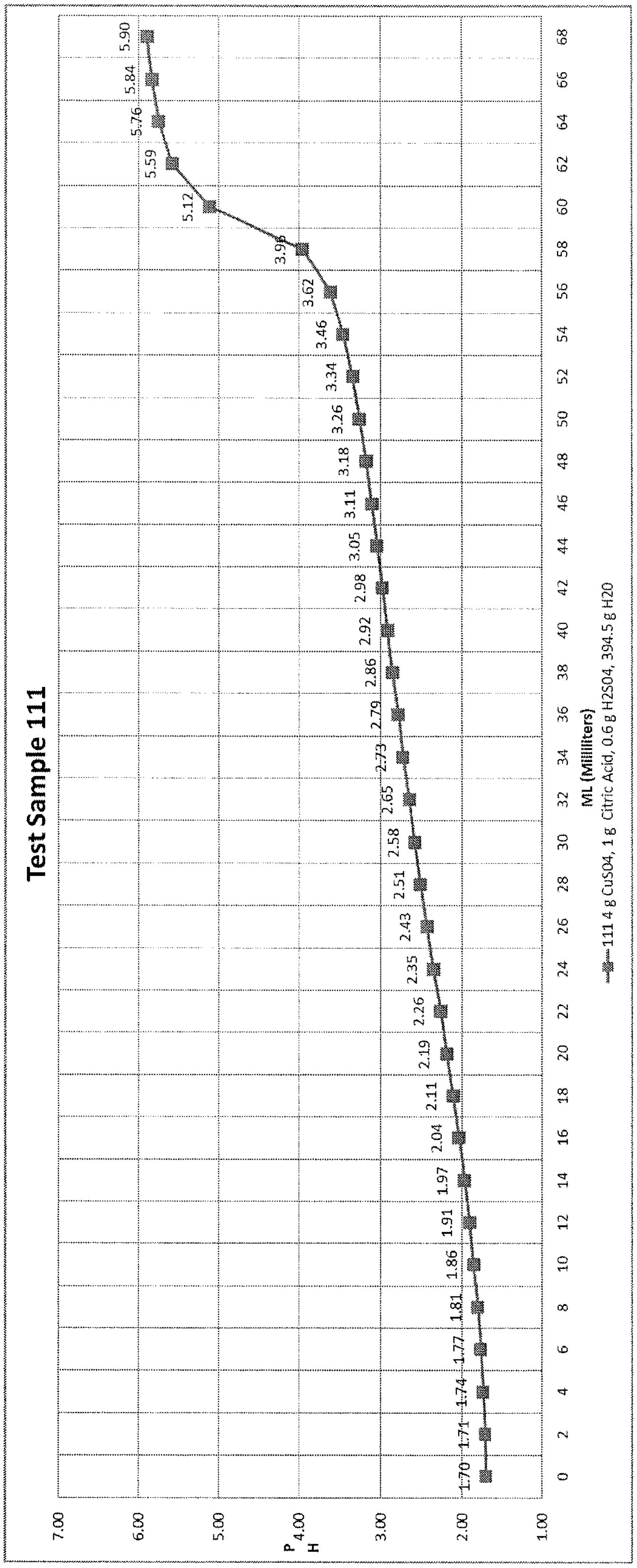
FIG. 10 is a graph of an exemplary pH titration curve (111) for a copper, citric acid and sulfuric acid mixture.
Figure 11:
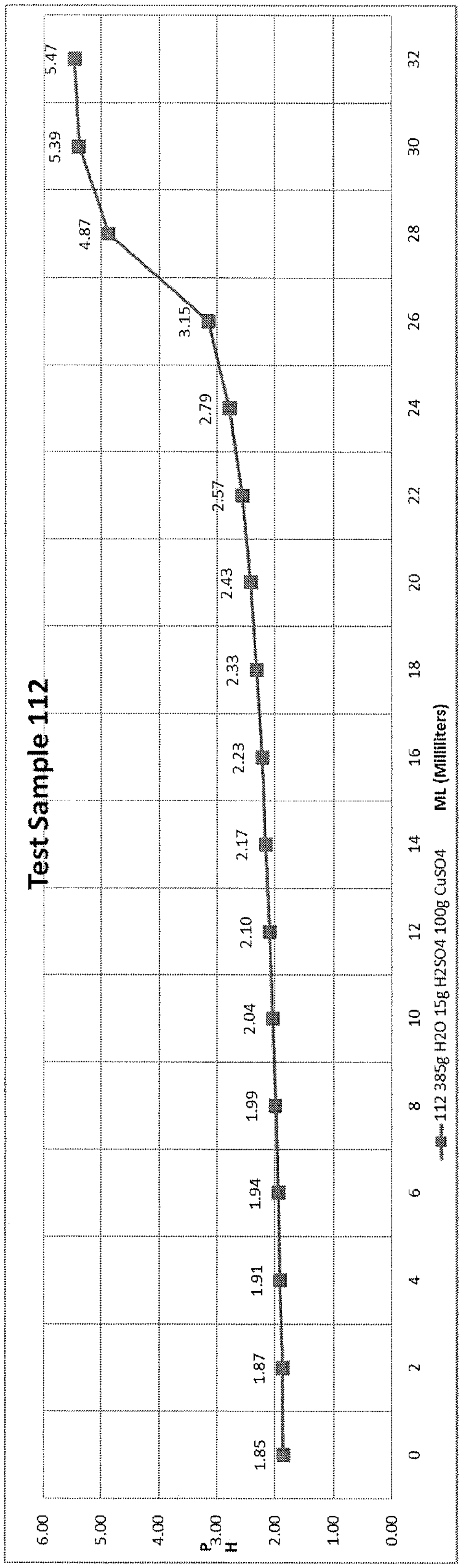
FIG. 11 is a graph of an exemplary pH titration curve (112) for a copper and sulfuric acid mixture.
Figure 12:
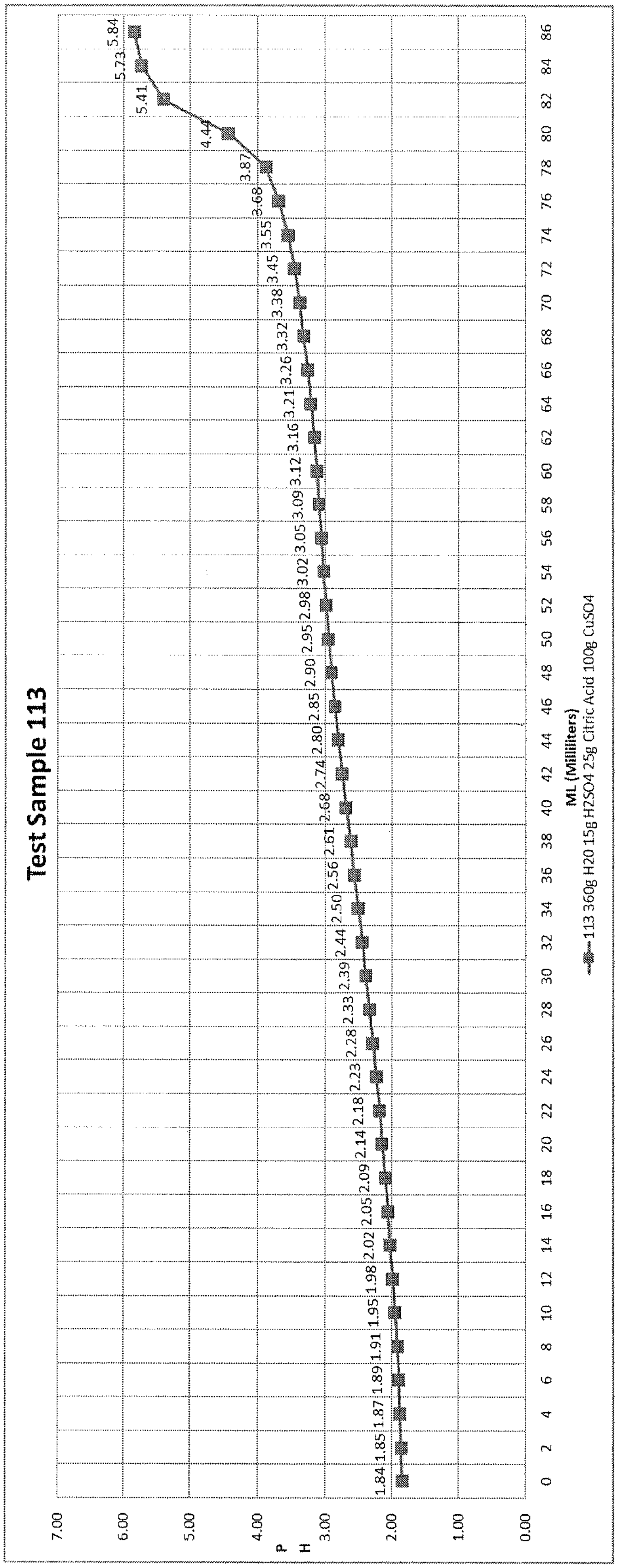
FIG. 12 is a graph of an exemplary pH titration curve (113) for a sulfuric acid, citric acid and copper mixture.
Figure 13:
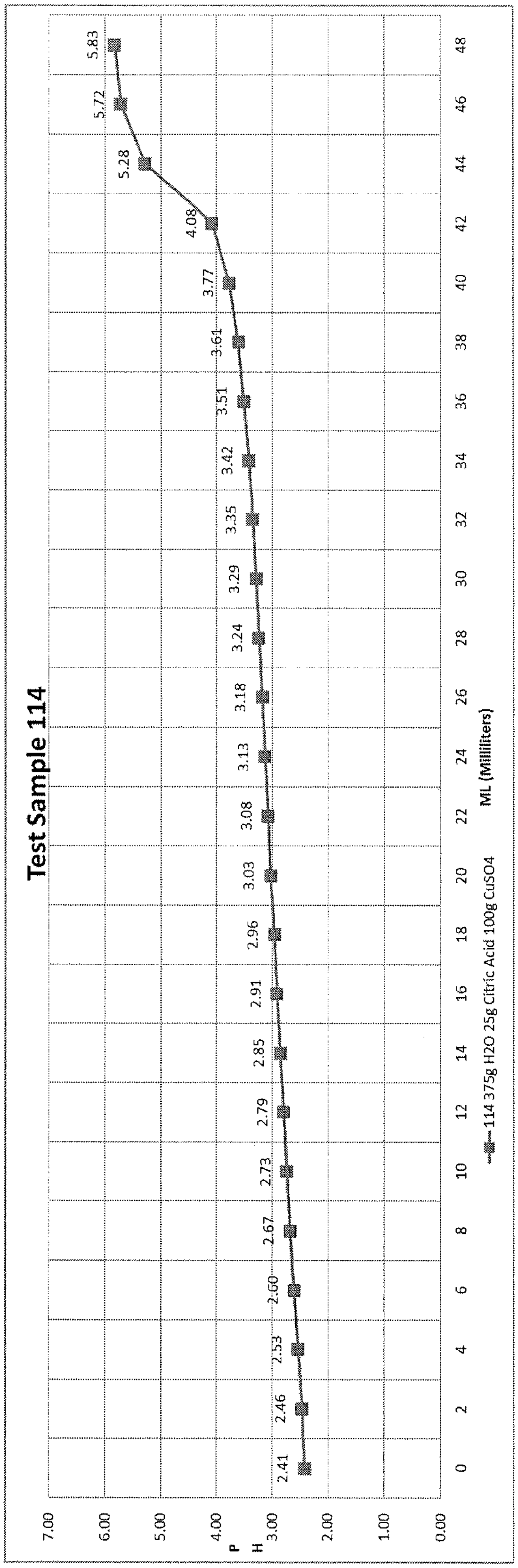
FIG. 13 is a graph of an exemplary pH titration curve (114) for a citric acid and copper mixture.
Figure 14:
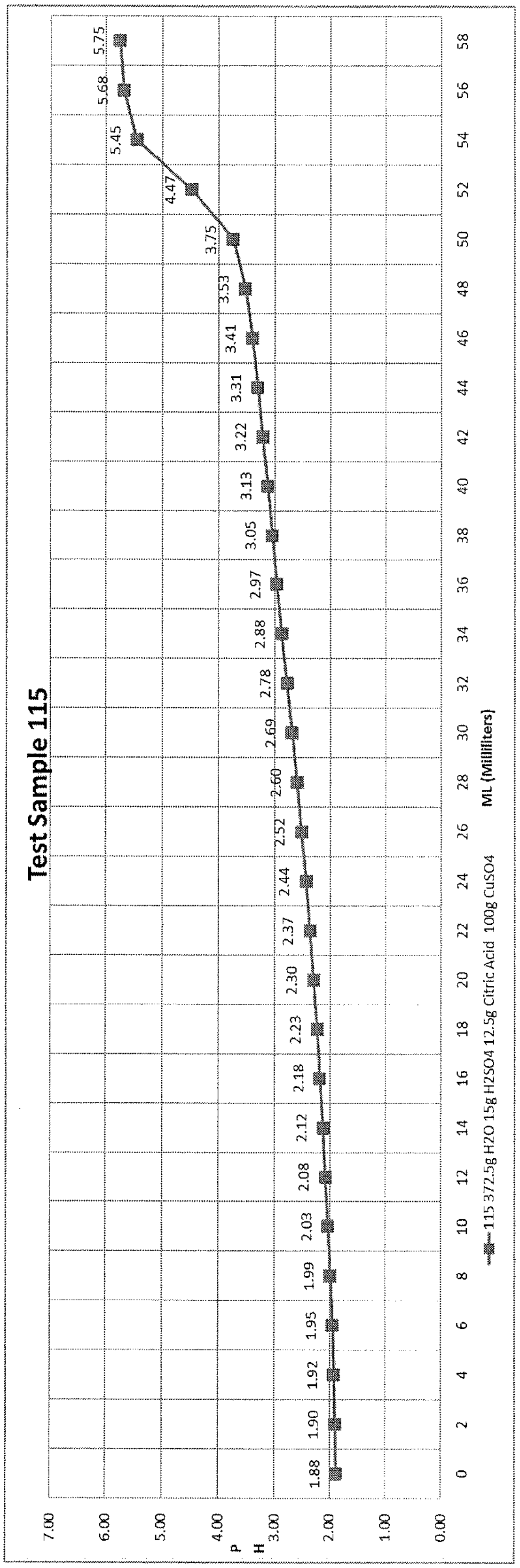
FIG. 14 is a graph of an exemplary pH titration curve (115) for a sulfuric acid, citric acid and copper mixture.
Figure 15:
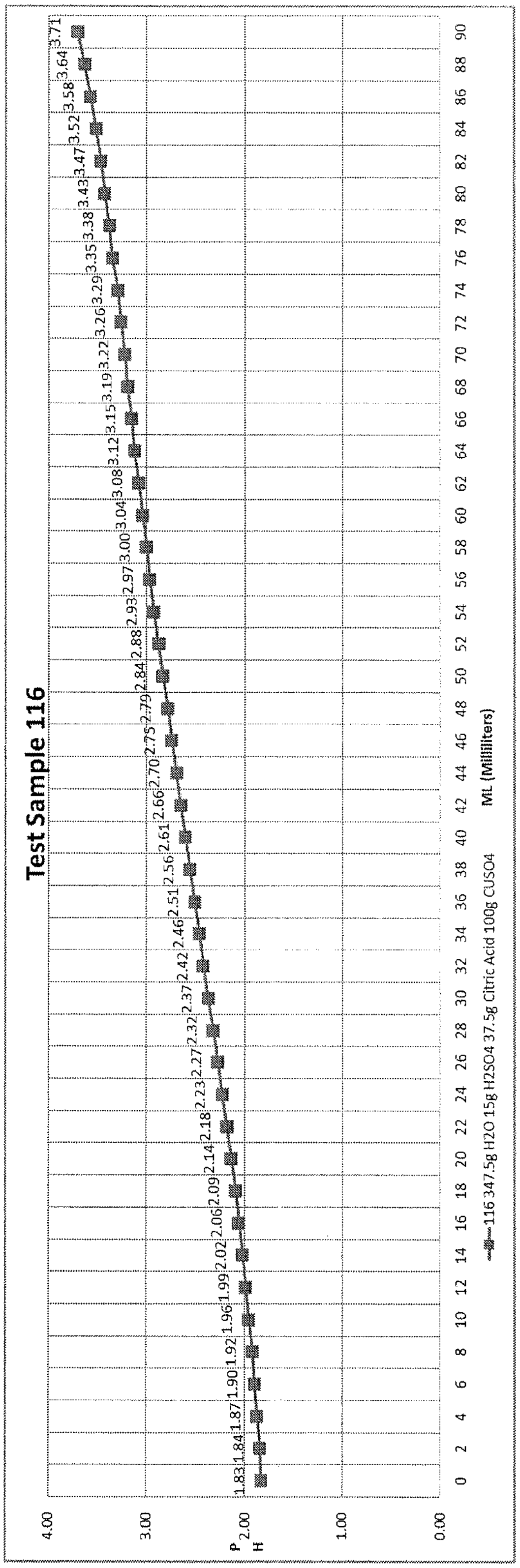
FIG. 15 is a graph of an exemplary pH titration curve (116) for a sulfuric acid, citric acid and copper mixture.
Figure 16:
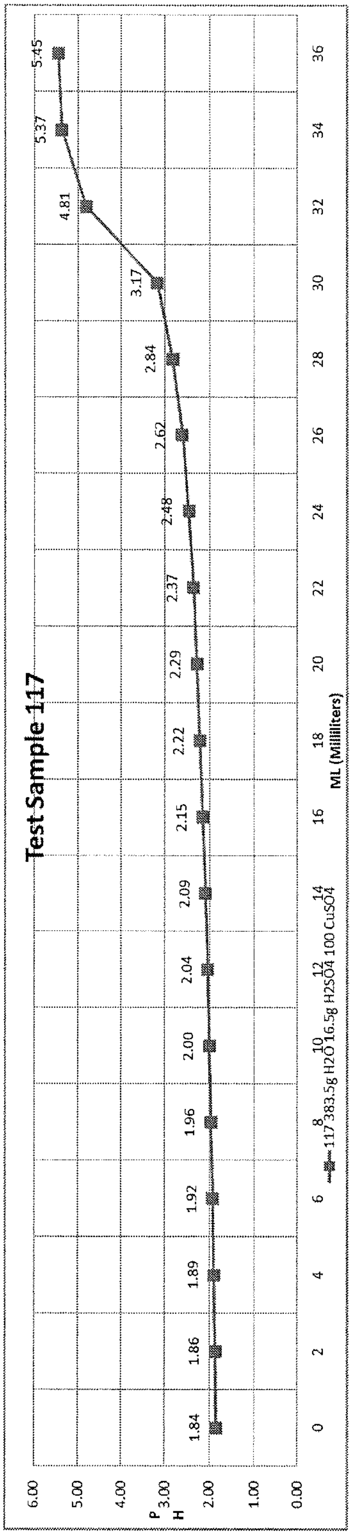
FIG. 16 is a graph of an exemplary pH titration curve (117) for a sulfuric acid mixture and copper.
Figure 17:
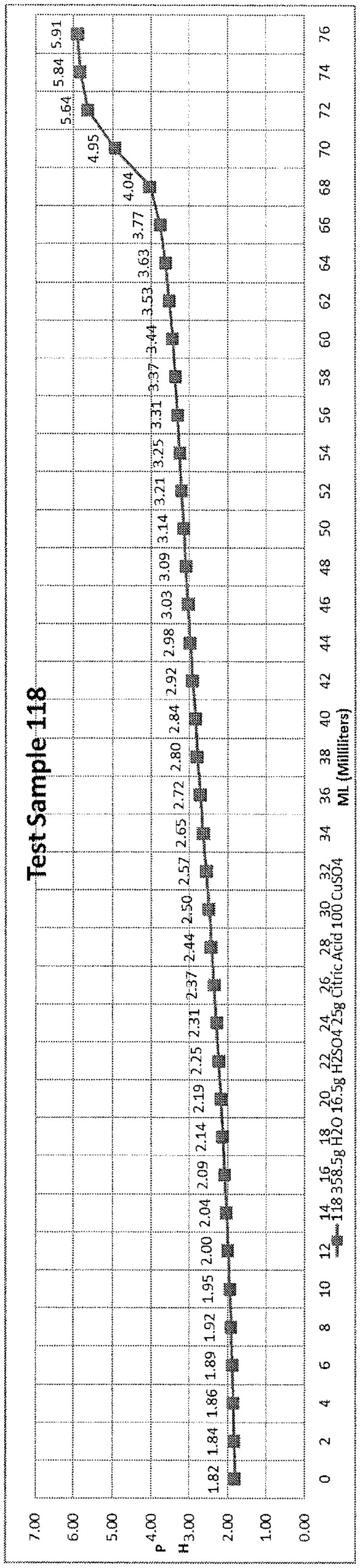
FIG. 17 is a graph of an exemplary pH titration curve (118) for a sulfuric acid, citric acid and copper mixture.
Figure 18:
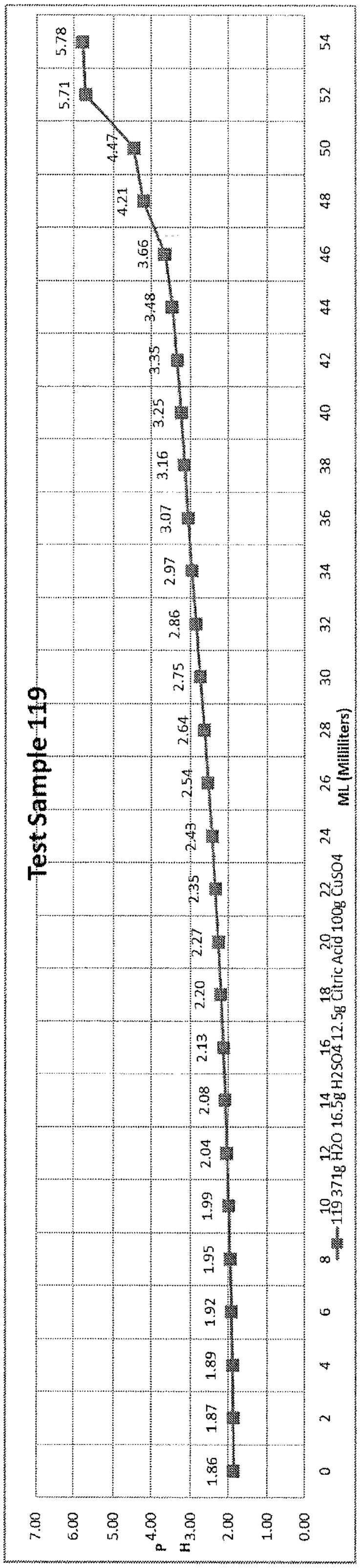
FIG. 18 is a graph of an exemplary pH titration curve (119) for a sulfuric acid, citric acid and copper mixture.
Figure 19:
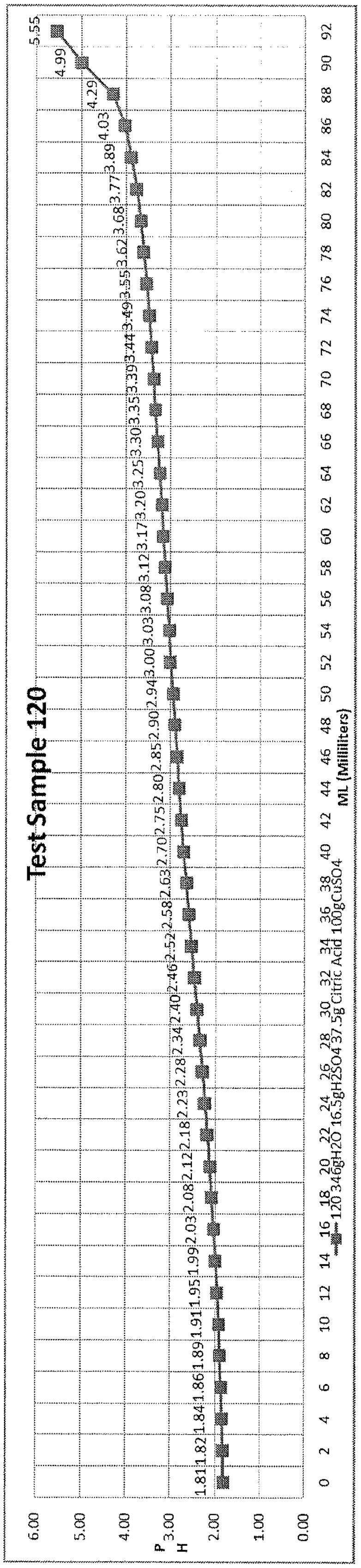
FIG. 19 is a graph of an exemplary pH titration curve (120) for a sulfuric acid, citric acid and copper mixture.
Figure 20:
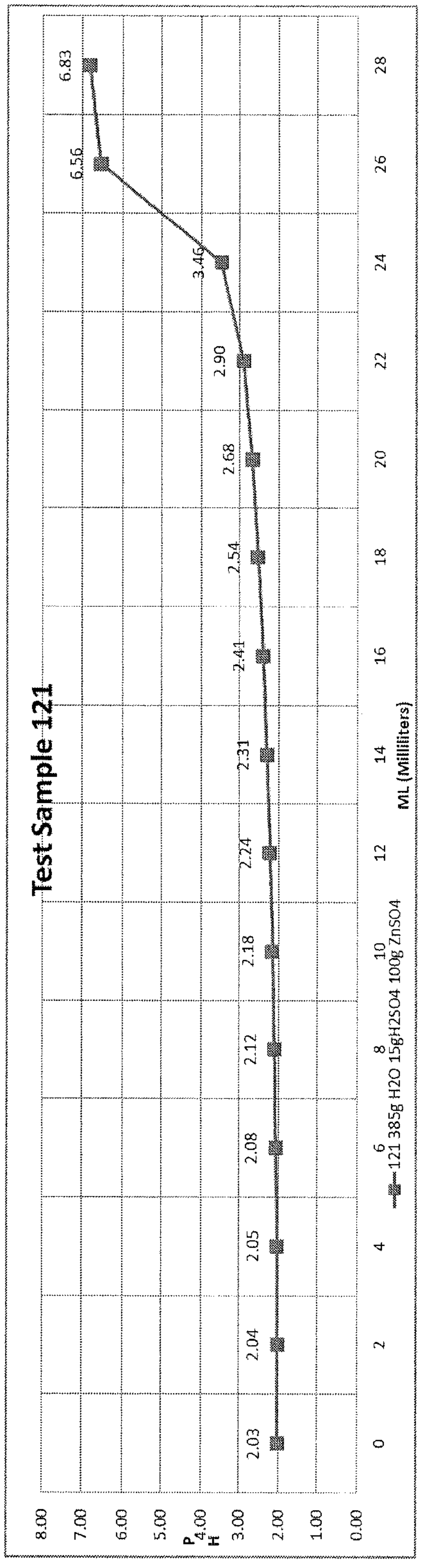
FIG. 20 is a graph of an exemplary pH titration curve (121) for a sulfuric acid, and zinc mixture.
Figure 21:
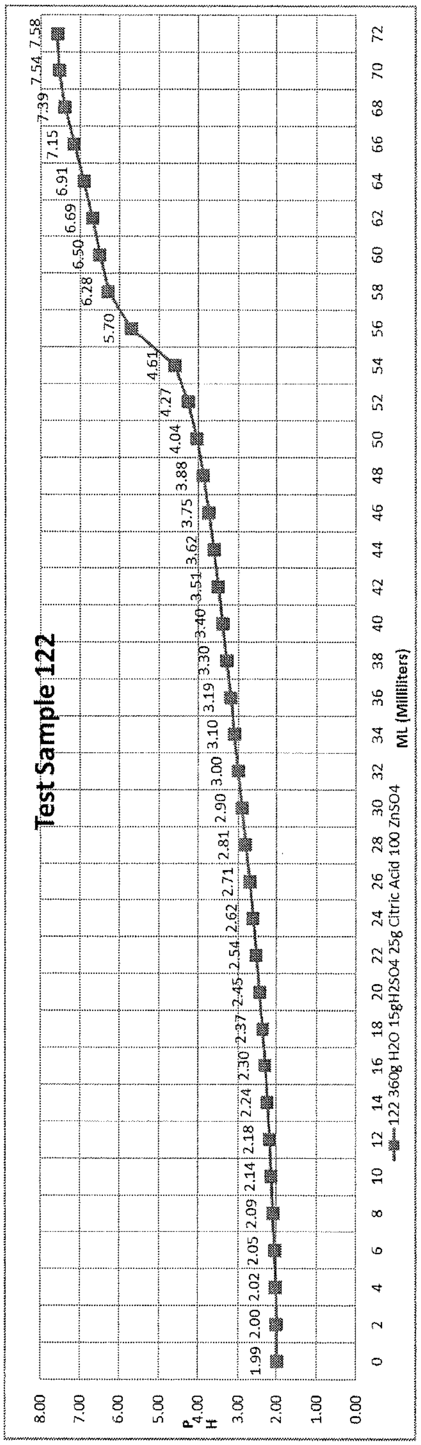
FIG. 21 is a graph of an exemplary pH titration curve (122) for a sulfuric acid, citric acid and zinc mixture.
Figure 22:
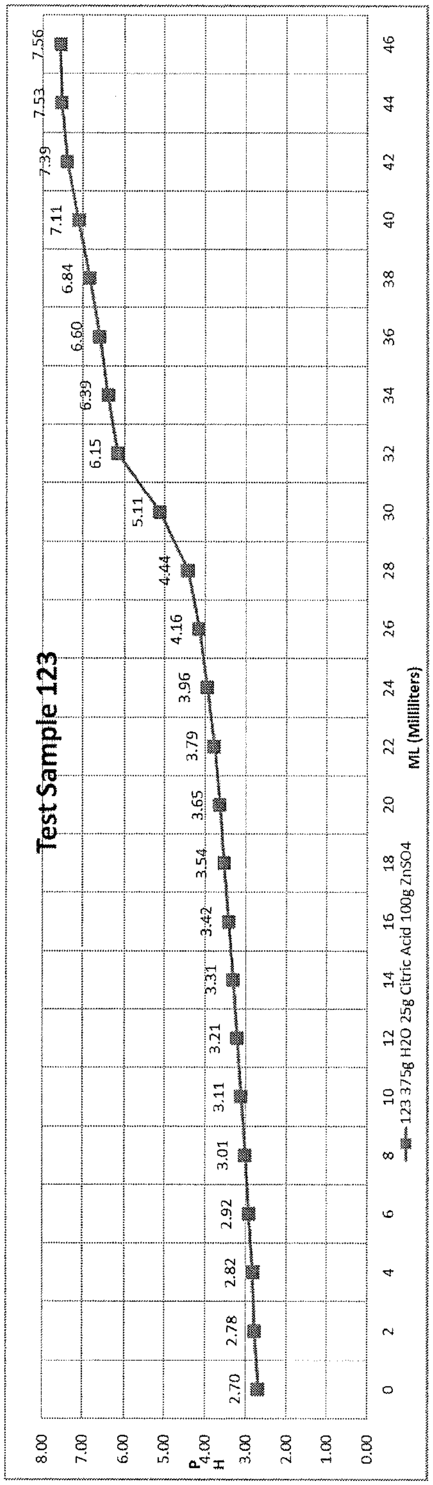
FIG. 22 is a graph of an exemplary pH titration curve (123) for a citric acid, and zinc mixture.
Figure 23:
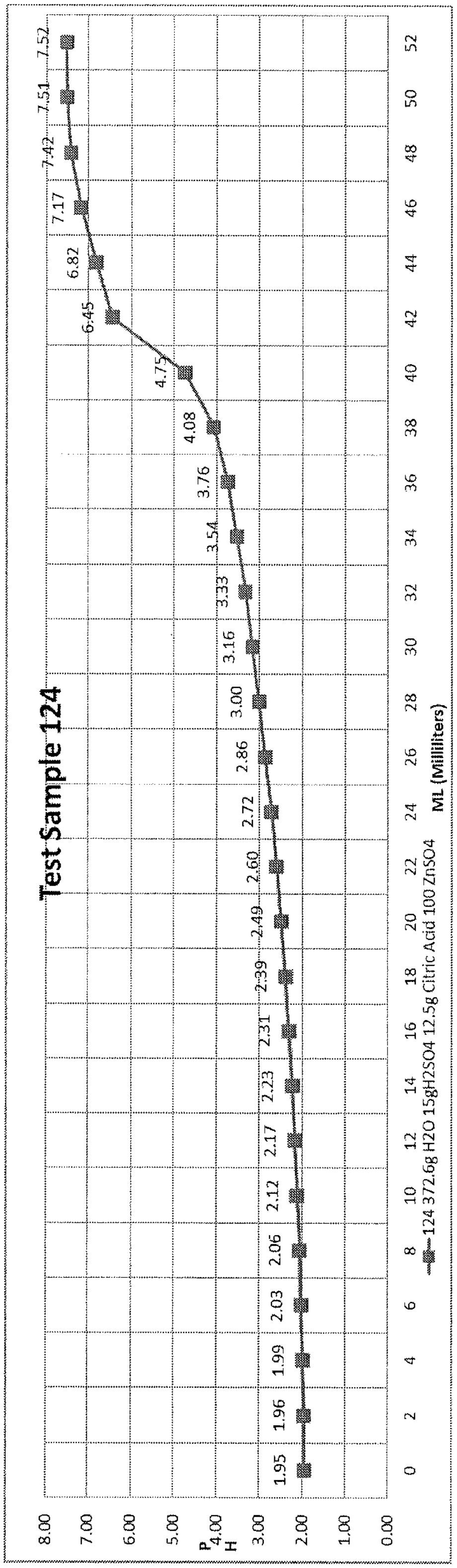
FIG. 23 is a graph of an exemplary pH titration curve (124) for a sulfuric acid, citric acid and zinc mixture.
Figure 24:
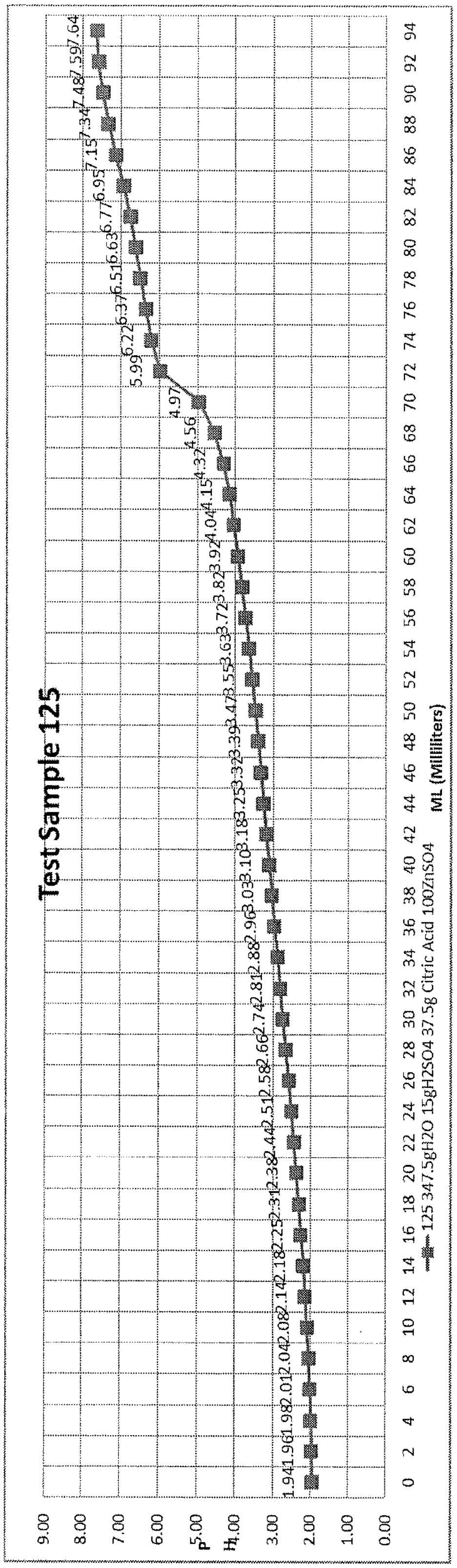
FIG. 24 is a graph of an exemplary pH titration curve (125) for a sulfuric acid, citric acid and zinc mixture.
Figure 25:
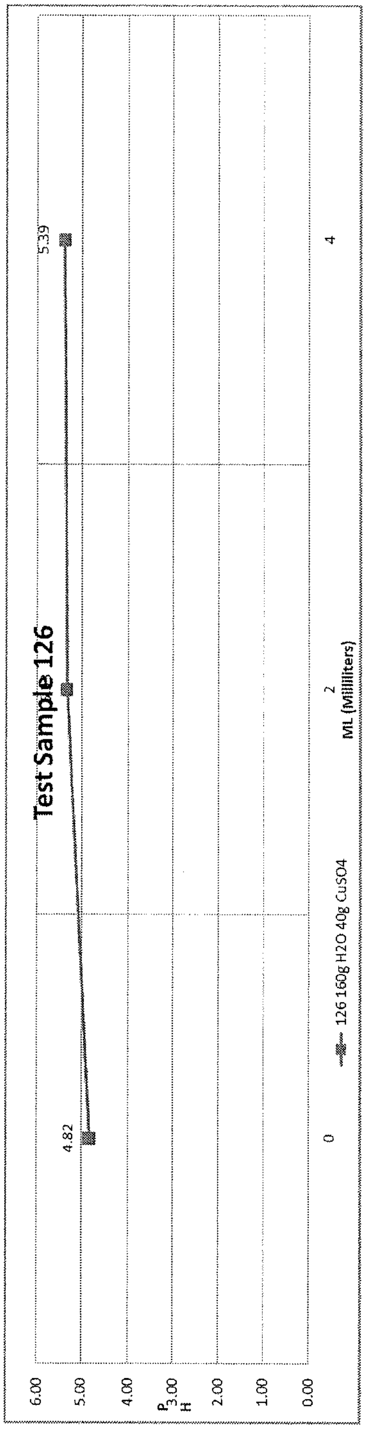
FIG. 25 is a graph of an exemplary pH titration curve (126) for a copper mixture.
Figure 26:
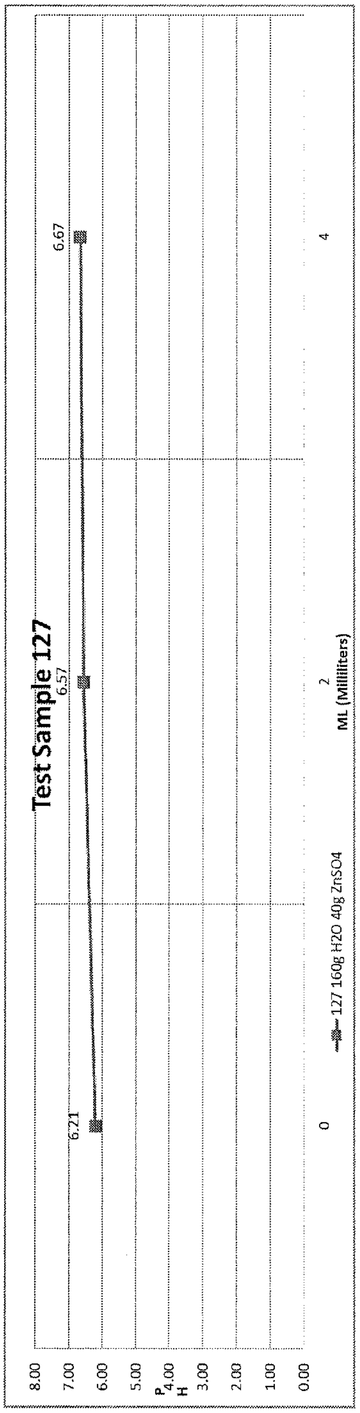
FIG. 26 is a graph of an exemplary pH titration curve (127) for a zinc mixture.
Figure 27:
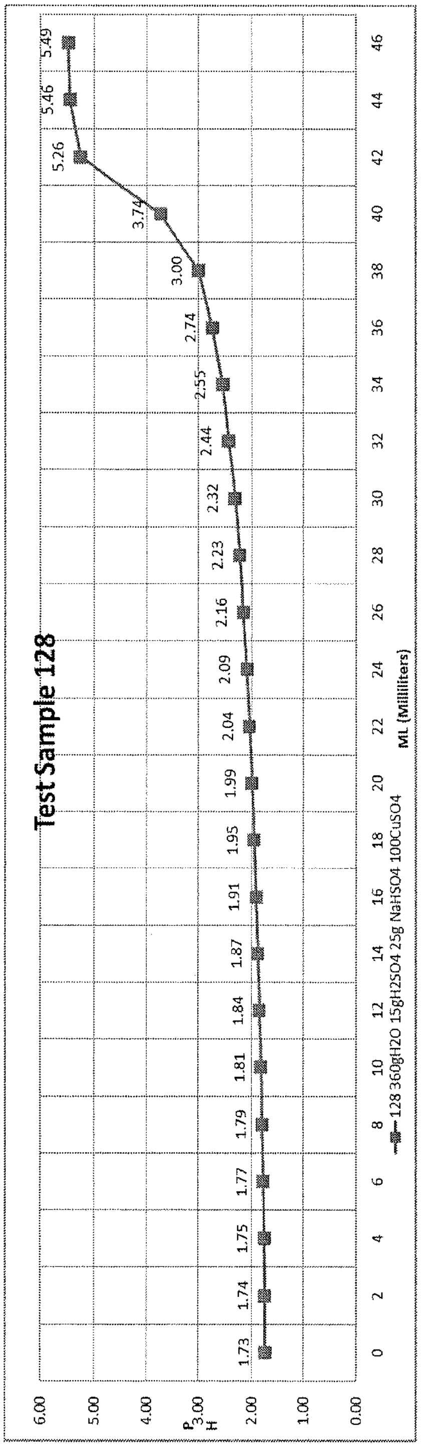
FIG. 27 is a graph of an exemplary pH titration curve (128) for a sulfuric acid, sodium and copper mixture.
Figure 28:
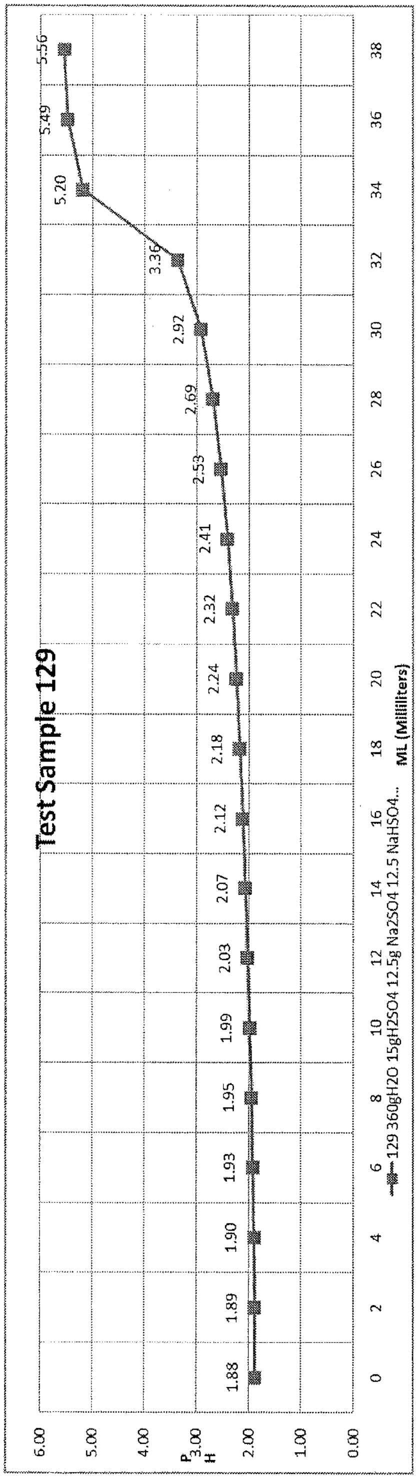
FIG. 28 is a graph of an exemplary pH titration curve (129) for a sulfuric acid and sodium mixture.
Figure 29:
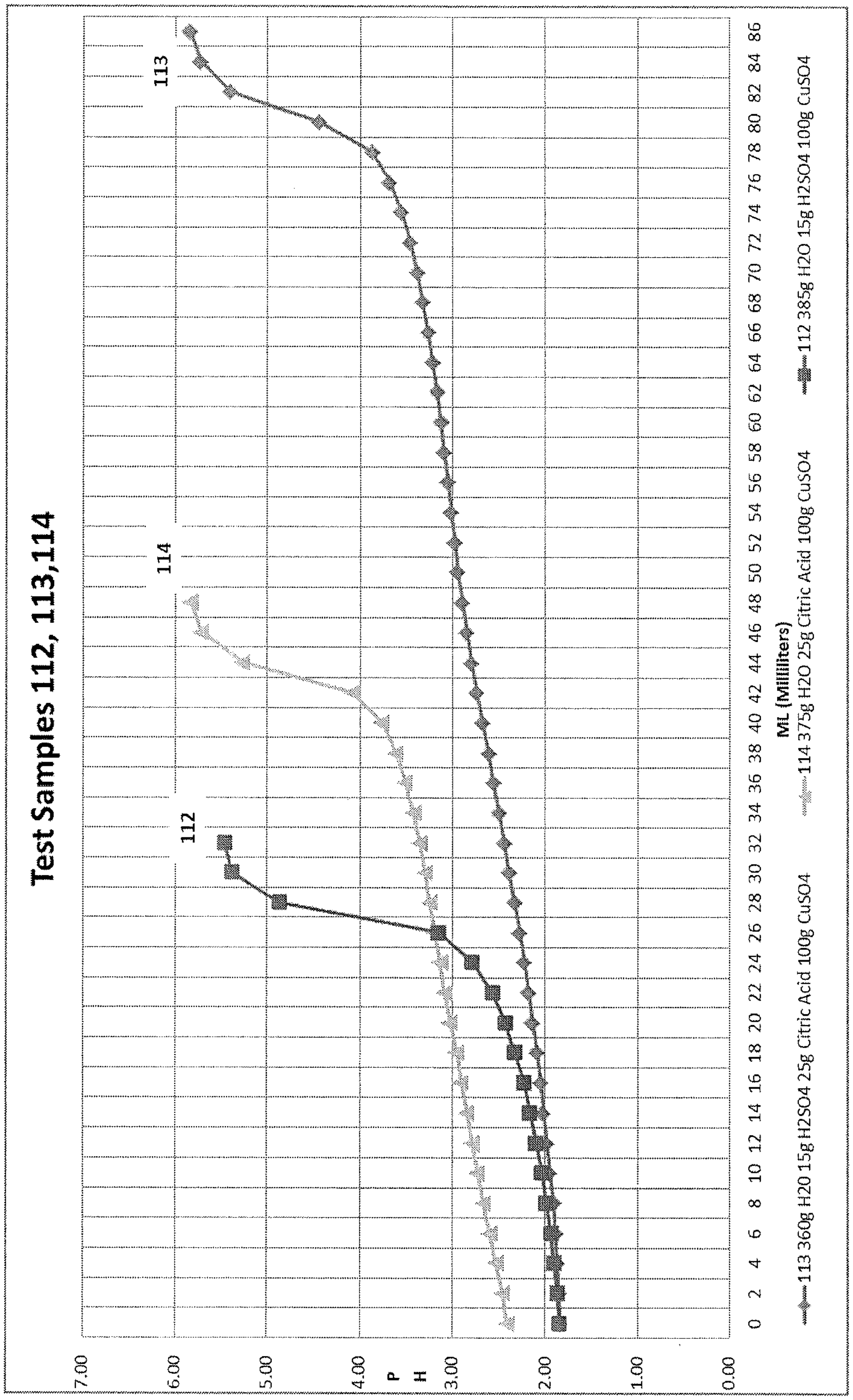
FIG. 29 is a combination graph showing each of the titration curves of FIGS. 11-13.
Figure 30:
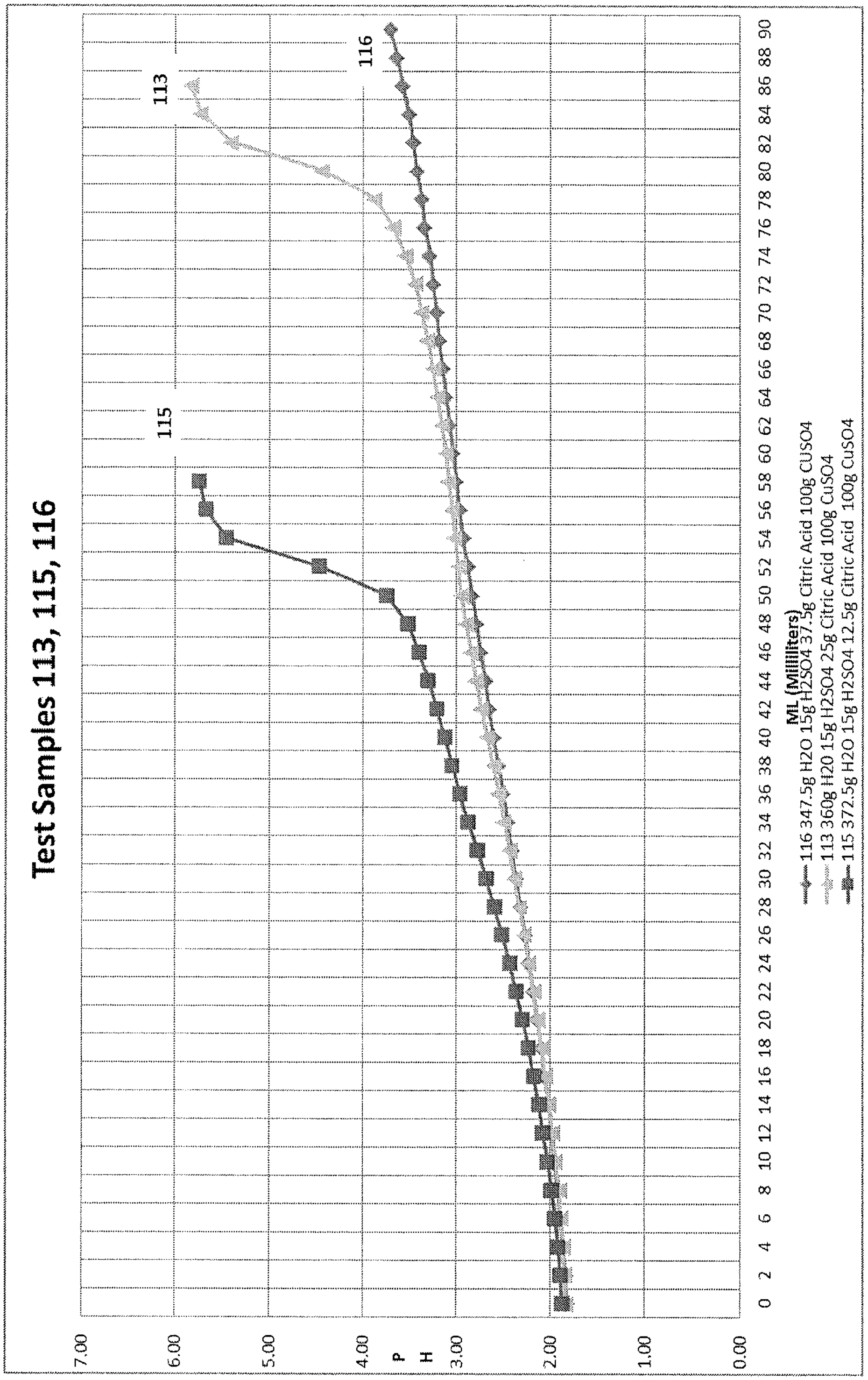
FIG. 30 is a combination graph showing each of the titration curves of FIGS. 12, 14 and 15.
Figure 31:
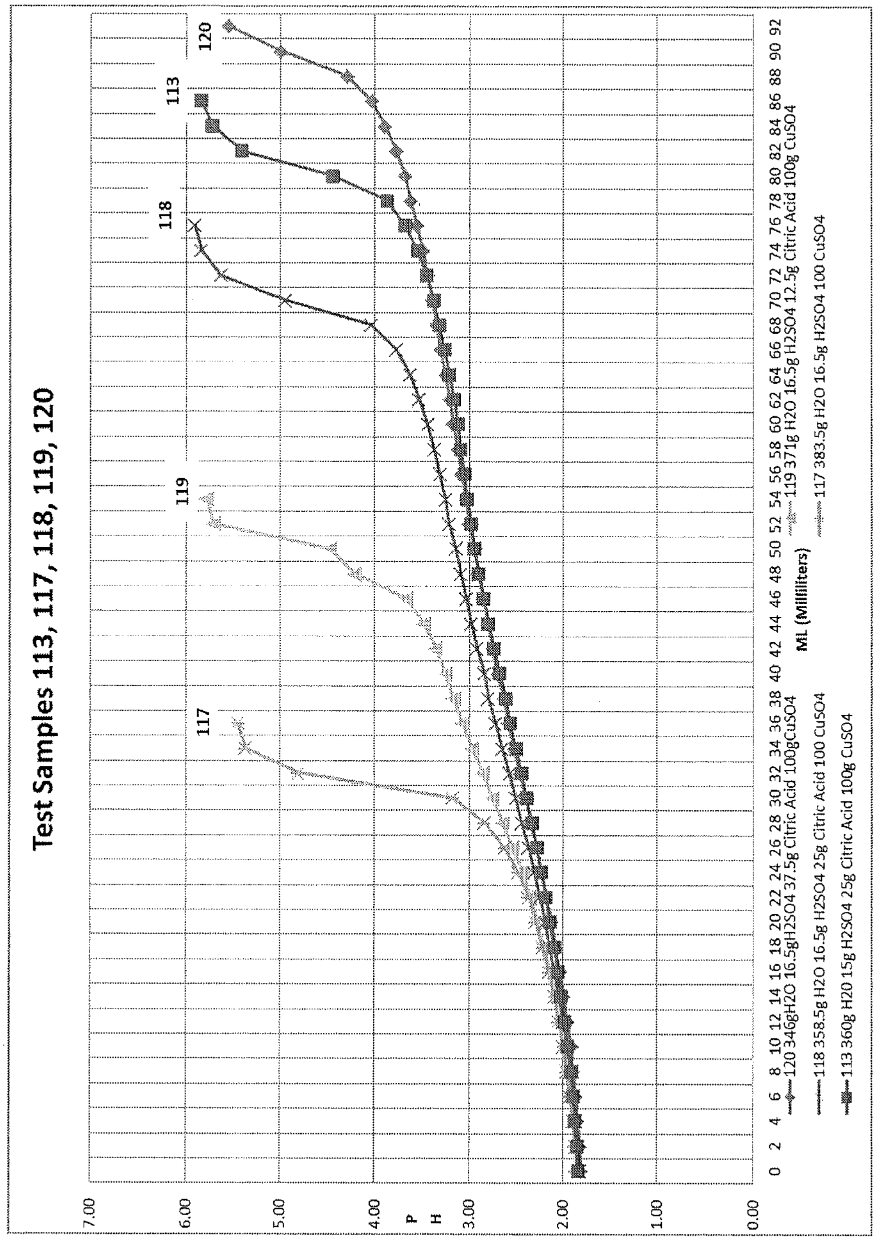
FIG. 31 is a combination graph showing each of the titration curves of FIGS. 12 and 16-19.
Figure 32:
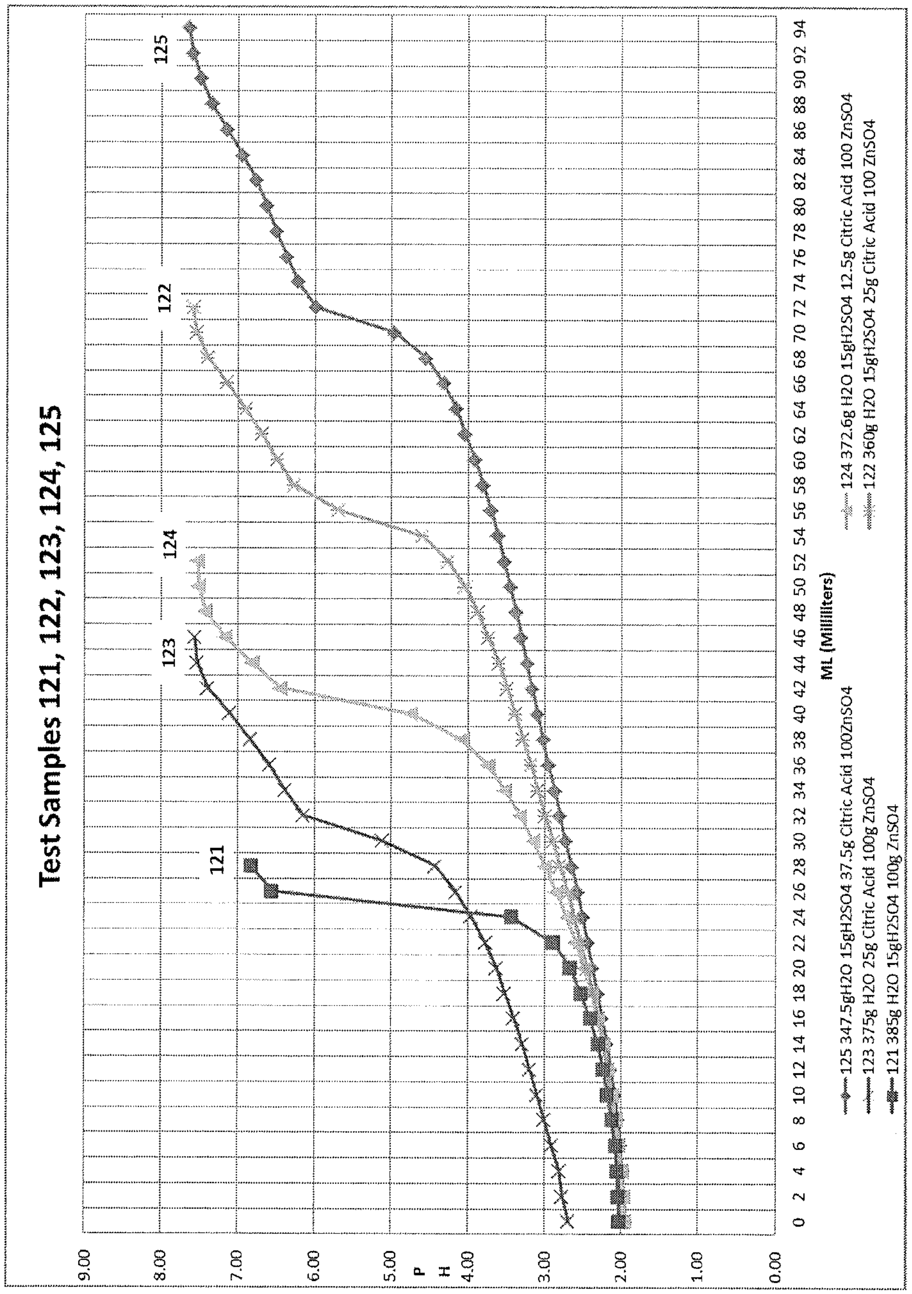
FIG. 32 is a combination graph showing each of the titration curves of FIGS. 20-24.
Figure 33:
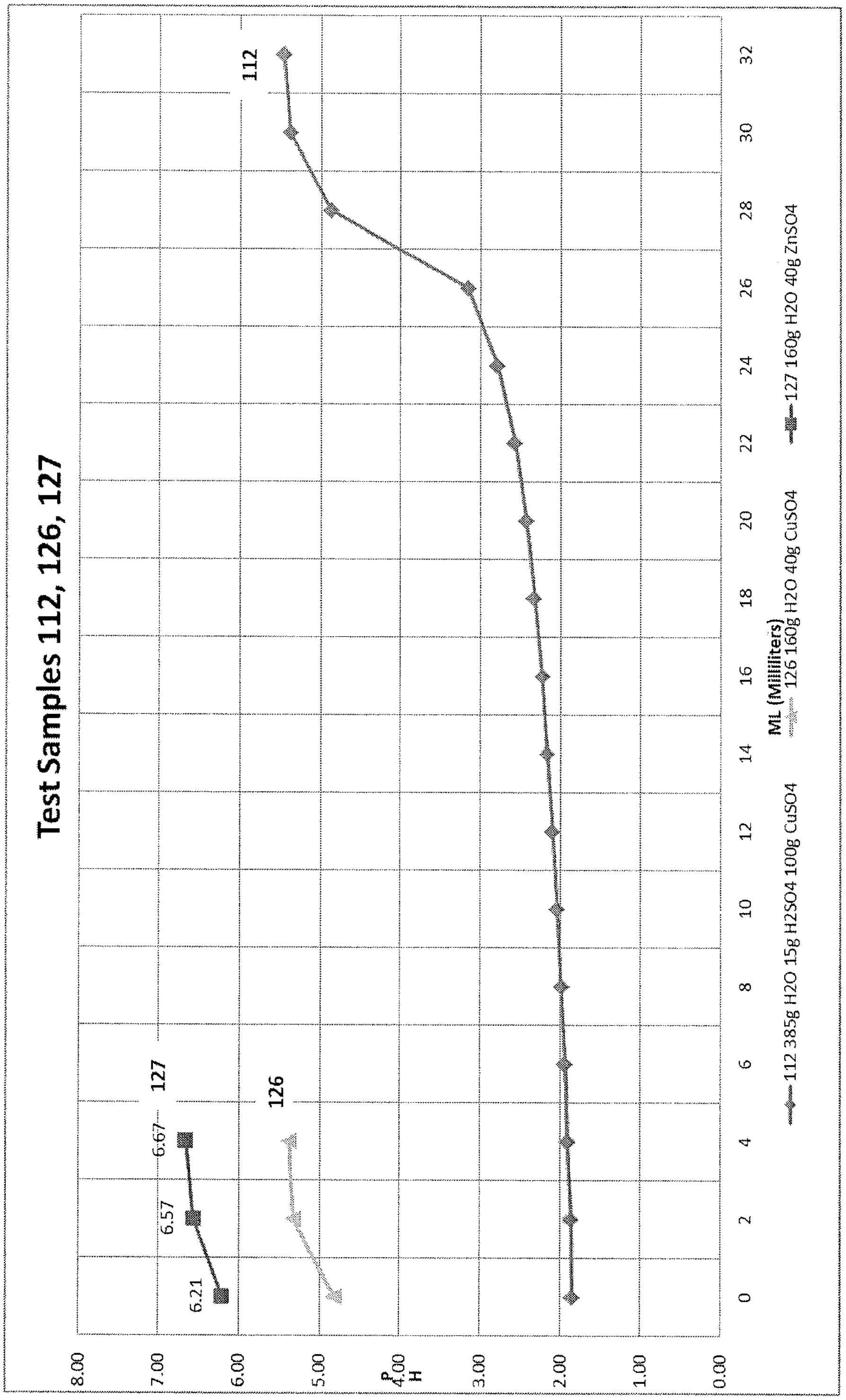
FIG. 33 is a combination graph showing each of the titration curves of FIGS. 11 and 25-26.
Figure 34:
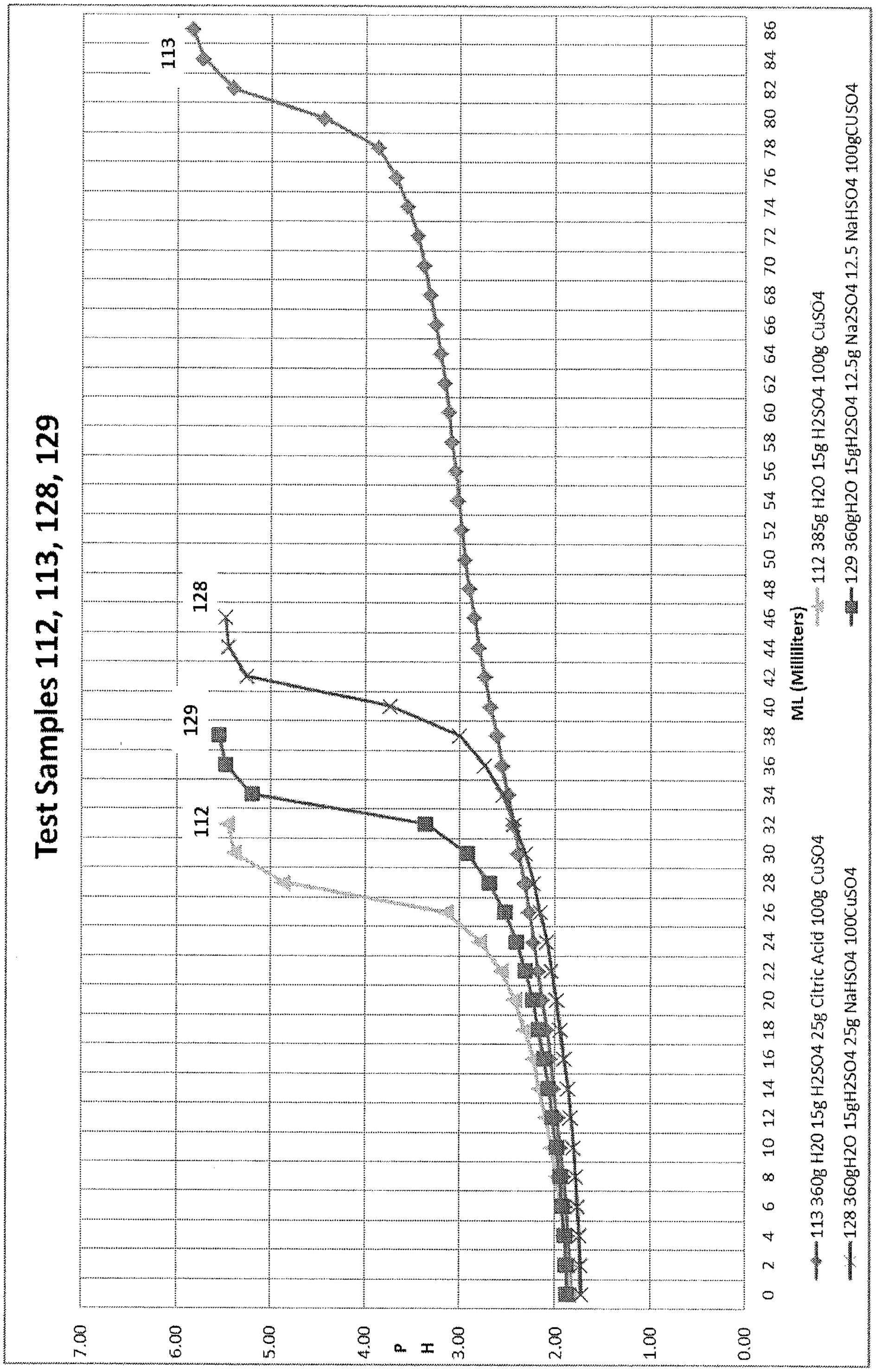
FIG. 34 is a combination graph showing each of the titration curves of FIGS. 11, 12, 27 and 28.

Set forth below in FIG. 7 is a combination of the graphs shown in FIGS. 1-6 (Test Samples 100-105) for comparison purposes, showing that the addition of citric acid to the compositions delays the increase in pH of the solution.

Compositions of the present invention were also used in separate experiments at commercial dairy operations.

Dairy Footbath Experiment 1:

In this exemplary experiment, a dairy foot bath having a volume of approximately 175 gallons was used. The composition added to the footbath had the same ingredients and the same ratios as example 3B (i.e., a composition comprising a mixture of 50 gm $CuSO_4{\cdot}H_2O$, 50 gm $ZnSO_4{\cdot}H_2O$, 15 gm $H_2SO_4$, 25 gm Citric Acid, and 360 gm $H_2O$). A sufficient quantity of this composition was added to the water in the 270-gallon foot bath to create a 5% solution.

The pH was then measured at 1.8. Thereafter, the foot bath was placed into use, and approximately 570 cows passed through it. The pH was then measured again, this time at 2.2. This was far below the level where the metal salts would otherwise precipitate from the solution. See Table 4 below.

TABLE 4

| 270 Gal. Foot Bath: $CuSO_4/ZnSO_4$ + Sulfuric acid + Citric acid pH of Foot Bath | |
|---|---|
| Start | End |
| 1.8 | 2.2 |

Dairy Footbath Experiment 2:

In this exemplary experiment, the dairy had two footbaths, each having a capacity of approximately 70 gallons. In the first (south) footbath, a composition comprising the same ingredients and ratios of example 3A without citric acid (i.e., a mixture of 50 gm $CuSO_{4.5}H_2O$, 50 gm $ZnSO_4{\cdot}H_2O$, 15 gm $H_2SO_4$, and 385 gm $H_2O$) was added to the water in this footbath to create a 5% solution. In the second (north) footbath, a composition comprising the same ingredients and ratios of example 3B including citric acid (i.e., a mixture of 50 gm $CuSO_{4.5}H_2O$, 50 gm $ZnSO_4{\cdot}H_2O$, 15 gm $H_2SO_4$, 25 gm Citric Acid, and 360 gm $H_2O$) was added to the water in this footbath to create a 5% solution.

The pH of both foot baths was initially measured at 1.78 for the first foot bath, and 1.72 for the second foot bath. Thereafter, both foot baths were placed into use and approximately 500 cows passed through each of them. The pH was then measured again at 4.95 for the first foot bath, and 4.29 for the second foot bath. The beginning and ending pH values are shown in Table 5 below. It can be seen that the second foot bath that included citric acid had higher resistance to increases in pH than the first foot bath which had no citric acid in its solution.

TABLE 5

| Foot Bath 1: $CuSO_4/ZnSO_4$, sulfuric acid pH of Bath | | Foot Bath 2: $CuSO_4/ZnSO_4$ + 3% sulfuric acid + 5% citric acid added pH of Bath | |
|---|---|---|---|
| Start | End | Start | End |
| 1.78 | 4.95 | 1.72 | 4.29 |

At the same dairy as Dairy Footbath Experiment 2 above, data was collected over of several months from a footbath having a composition comprising the same ingredients and ratios of example 3B including citric acid (i.e., a mixture of 50 gm $CuSO_{4.5}H_2O$, 50 gm $ZnSO_4{\cdot}H_2O$, 15 gm $H_2SO_4$, 25 gm Citric Acid, and 360 gm $H_2O$) added to the water in the footbath to create a 5% solution. Samples were taken at three different times: (a) at the beginning of use (fresh footbath), (b) at a midpoint, when approximately half of the cows expected to use the footbath had gone through it, and (c) at an endpoint, just prior to replacement of the footbath solution. The averages and standard deviations for these data are set forth in table 5A below.

TABLE 5A

| | BEGINNING | MIDPOINT | ENDPOINT |
|---|---|---|---|
| Average pH | 2.09 | 2.03 | 2.15 |
| Standard Deviation | ±0.23 | ±0.25 | ±0.26 |

Dairy Footbath Experiment 3:

In this exemplary experiment, the same two 70-gallon foot baths were used. In the first (south) foot bath, a solution having the same composition as in dairy experiment 2 above (i.e., a mixture of 50 gm $CuSO_{4.5}H_2O$, 50 gm $ZnSO_4{\cdot}H_2O$, 15 gm $H_2SO_4$, and 385 gm $H_2O$) was added to the water in this footbath to create a 5% solution. However, in the second (north) footbath, a mixture having the same composition as in dairy experiment 2 above, including citric acid, was used except that the concentration of sulfuric acid was 3.3% instead of 3% (i.e., a mixture of 50 gm $CuSO_4{\cdot}5H_2O$, 50 gm $ZnSO_4{\cdot}H_2O$, 16.5 gm $H_2SO_4$, 25 gm Citric Acid, and 358.5 gm $H_2O$). This mixture was added to the second foot bath to create a 5% solution.

The pH of both foot baths was measured at 1.70 for the first foot bath, and 1.6 for the second foot bath. Thereafter, both foot baths were placed into use and approximately 500 cows passed through each of them. The pH was then measured again at 5.0 for the first foot bath, and 3.64 for the second foot bath as shown in Table 6 below. It can be seen that the second foot bath that included citric acid with a higher concentration of sulfuric acid had even higher resistance to increases in pH.

TABLE 6

| Foot Bath 1: $CuSO_4/ZnSO_4$, sulfuric acid pH of Bath | | Foot Bath 2: $CuSO_4/ZnSO_4$ + 3.3% sulfuric acid + 5% citric acid added pH of Bath | |
|---|---|---|---|
| Start | End | Start | End |
| 1.70 | 5.0 | 1.6 | 3.64 |

OTHER EXPERIMENTS

Set forth in FIGS. 8-34 (Test Samples 109-129 and comparison charts) are the results of other laboratory experiments which could be adapted for use in bovine foot baths showing the effectiveness of the inclusion of quantities of citric acid alone and with sulfuric acid to slow the rise of pH as ammonium hydroxide is added, simulating the neutralizing effect of alkaline compounds in the animal waste deposited in actual foot bath water. Each graph shows the initial ingredients and pH of the composition, and a titration graph showing the increase in pH as doses of 2 ml ammonium hydroxide 1.25% solution are added.

It is to be appreciated that the data shown in Test Sample 111, for example, illustrates the fundamental benefits provided by the compositions of the present invention.

It is to be appreciated that different versions of the invention may be made from different combinations of the various features described above. It is to be understood that other variations and modifications of the present invention may be made without departing from the scope thereof. It is also to be understood that the present invention is not to be limited by the specific embodiments or examples disclosed herein, but only in accordance with the appended claims when read in light of the foregoing specification.

What is claimed:

1. A composition for use in a livestock foot bath which helps maintain the solubility of dissolved metal ions comprising an aqueous solution containing at least one of a copper salt and a zinc salt; a strong inorganic acid; and at least one organic polyprotic acid in a concentration of between about 1% wt/wt to about 10% wt/wt, the concentration being sufficient to inhibit copper and zinc ions from precipitating out of said composition when said composition is fouled by organic waste in said livestock foot bath.

2. The composition of claim 1 wherein said at least one of a copper salt and a zinc salt is present in an amount of about 1% wt/wt to about 35% wt/wt.

3. The composition of claim 1 wherein said at least one of a copper salt or a zinc salt is provided in a concentration of between about 5% wt/wt and about 20% wt/wt.

4. The composition of claim 1 wherein said copper salt is present in an amount of about 1% wt/wt to about 15% wt/wt.

5. The composition of claim 1 wherein said zinc salt is present in an amount of about 1% wt/wt to about 15% wt/wt.

6. The composition of claim 1 wherein said at least one organic polyprotic acid is provided in a concentration of between about 4% and about 6% wt/wt in said aqueous solution.

7. The composition of claim 1 wherein said at least one organic polyprotic acid comprises citric acid.

8. The composition of claim 1, wherein said strong inorganic acid is present in an amount from about 1% wt/wt to about 10% wt/wt in said aqueous solution.

9. The composition of claim 1, wherein said strong inorganic acid is present in an amount from about 2.5% wt/wt to about 4% wt/wt in said aqueous solution.

10. A method for increasing the useful life of a livestock foot bath by inhibiting the precipitation of metal salts therein comprising the steps of:

preparing an aqueous solution for said foot bath including at least one of a copper sulfate compound or a zinc sulfate compound;

a strong inorganic acid; and at least one organic polyprotic acid in a concentration between about 1% wt/wt to about 10% wt/wt, the concentration being sufficient to inhibit copper and zinc ions from precipitating out of said aqueous solution when said aqueous solution is fouled by organic waste in said livestock foot bath.

11. The method of claim 10 wherein said at least one of a copper salt and a zinc salt is present in an amount of about 1% wt/wt to about 35% wt/wt.

12. The method of claim 10 wherein said at least one of a copper salt or a zinc salt is provided in a concentration of between about 5% wt/wt and about 20% wt/wt.

13. The method of claim 10 wherein said at least one organic polyprotic acid is citric acid.

14. The method of claim 10 wherein said at least one organic polyprotic acid is provided in a concentration of between about 4% and about 6% wt/wt in said aqueous solution.

15. The method of claim 10 wherein said strong inorganic acid is present in an amount from about 1% wt/wt to about 10% wt/wt in said aqueous solution.

16. The method of claim 10 wherein said strong inorganic acid is present in an amount from about 2.5% wt/wt to about 4% wt/wt in said aqueous solution.

17. A composition for use in a livestock foot bath which helps maintain the solubility of dissolved metal ions comprising an aqueous solution including at least one of a copper salt or a zinc salt; and at least one organic polyprotic acid present in a concentration between about 1% wt/wt to about 10% wt/wt, the concentration being sufficient to inhibit copper and zinc ions from precipitating out of said composition when said composition is fouled by organic waste in said livestock foot bath.

18. The composition of claim 17 further comprising a strong inorganic acid in a concentration of up to about 10.0%.

19. The composition of claim 18 wherein the weight ratio of the at least one of a copper salt or a zinc salt to the strong inorganic acid is in a range of about 1:1 to about 10:1.

20. The composition of claim 18 wherein the weight ratio of the strong inorganic acid to the at least one organic polyprotic acid is in a range of about 1:1 to about 1:10.

21. The composition of claim 18 wherein the weight ratio of the strong inorganic acid to the at least one organic polyprotic acid is in a range of about 1:1 to about 1:3.

* * * * *